(12) United States Patent
Bee et al.

(10) Patent No.: US 7,425,417 B2
(45) Date of Patent: Sep. 16, 2008

(54) DETECTION OF HIV-1 BY NUCLEIC ACID AMPLIFICATION

(75) Inventors: Gary G. Bee, Vista, CA (US); Yeasing Y. Yang, San Diego, CA (US); Dan Kolk, Ramona, CA (US); Cristina Giachetti, Solana Beach, CA (US); Sherrol H. McDonough, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 56 days.

(21) Appl. No.: 11/492,532

(22) Filed: Jul. 24, 2006

(65) Prior Publication Data

US 2007/0015142 A1 Jan. 18, 2007

Related U.S. Application Data

(62) Division of application No. 10/632,658, filed on Aug. 1, 2003, now Pat. No. 7,097,979, which is a division of application No. 09/611,627, filed on Jul. 7, 2000, now Pat. No. 6,623,920.

(60) Provisional application No. 60/143,072, filed on Jul. 9, 1999.

(51) Int. Cl.
*C12Q 1/68* (2006.01)
*C07H 21/02* (2006.01)
*C07H 21/04* (2006.01)

(52) U.S. Cl. ............... 435/6; 536/23.1; 536/24.3

(58) Field of Classification Search ............... 435/6; 536/23.1, 24.3
See application file for complete search history.

(56) References Cited

U.S. PATENT DOCUMENTS

| | | | |
|---|---|---|---|
| 5,399,491 A | 3/1995 | Kacian et al. | |
| 5,629,413 A | 5/1997 | Peterson et al. | |
| 5,840,480 A | 11/1998 | Guertler et al. | |
| 6,096,538 A | 8/2000 | Kingsman et al. | |
| 6,300,075 B1 | 10/2001 | Preston et al. | |
| 6,303,293 B1 | 10/2001 | Patterson et al. | |
| 6,610,476 B1 | 8/2003 | Chang et al. | |
| 6,623,919 B1 | 9/2003 | Gorman et al. | |
| 6,623,920 B1 | 9/2003 | Bee et al. | |
| 6,649,749 B2 | 11/2003 | McDonough et al. | |
| 7,030,234 B2 | 4/2006 | Mauclere et al. | |
| 7,097,979 B2 | 8/2006 | Bee et al. | |

FOREIGN PATENT DOCUMENTS

| | | |
|---|---|---|
| EP | 0481215 A1 | 4/1992 |
| EP | 0727497 B1 | 8/1996 |
| EP | 0887427 B1 | 12/1998 |
| WO | 98/50583 A1 | 11/1998 |
| WO | 99/07898 A1 | 2/1999 |

OTHER PUBLICATIONS

Fransen K., et al., "Design and Evaluation of new, highly sensitive and specific primers for polymerase chain reaction detection of HIV-1 infected primary lymphocytes", Mol. Cell. Probes, 1994, pp. 317-322, vol. 8 (4), Academic Press Limited.
Dolan, J. et al, "Construction of gag, pol, and env specific riboprobes for confirmation of HIV-1 specific polymerase chain reaction products" J. Virol. Methods, 1994, pp. 167-175, vol. 48 (2-3), Elsevier Science B.V.
Billyard et al."Early Detection of HIV-1 RNA with Transcription Mediated Amplification", Transfusion, 37(9): S386 (1997) (Abstract XP000980447) USA.
Bush et al."Detection of Human Immunodeficiency Virus Type 1 RNA in Plasma Samples . . . ", J.Clin. Microbiol.,vol. 30, No. 2, p. 281-286, (1992) USA.
C. Giachetti et al., Highly Sensitive Multiplex Assay for . . . , J.Clin. Microbiol., vol. 40, No. 7, p. 2408-2419, (Jul. 2002), American Society of Microbiology, USA.

*Primary Examiner*—Ethan Whisenant
(74) *Attorney, Agent, or Firm*—Christine A. Gritzmacher

(57) ABSTRACT

Nucleic acid sequences and methods for detecting HIV-1 nucleic acid (LTR and pol sequences) in biological samples by detecting amplified nucleic acids are disclosed. Kits comprising nucleic acid oligomers for amplifying HIV-1 nucleic acid present in a biological sample and detecting the amplified nucleic acid are disclosed.

20 Claims, 4 Drawing Sheets

HIV-LTR

**HIV-*pol***

DETECTION OF HIV-1 BY NUCLEIC ACID AMPLIFICATION

RELATED APPLICATIONS

This application is a divisional of application Ser. No. 10/632,658, filed Aug. 1, 2003, now U.S. Pat. No. 7,097,979, which is a divisional of application Ser. No. 09/611,627, filed Jul. 7, 2000, now U.S. Pat. No. 6,623,920, and claims the benefit under 35 U.S.C. 119(e) of provisional application No. 60/143,072, filed Jul. 9,1999, which are all incorporated by reference.

GOVERNMENT RIGHTS

This invention was made with United States government support under contract NO1-AB-67130 awarded by the National Institutes of Health. The government has certain rights in the invention

FIELD OF THE INVENTION

This invention relates to diagnostic detection of viral nucleic acids, and specifically relates to compositions and assays for detecting HIV-1 sequences using transcription-mediated nucleic acid amplification and probe detection of amplified sequences.

BACKGROUND OF THE INVENTION

Human immunodeficiency virus 1 (HIV-1) is the causative agent of acquired immunodeficiency syndrome (AIDS) and AIDS related syndrome (ARC). Because the infectious virus is transmissible in body fluids, including blood and plasma, it is important to detect infected body fluids before antibodies to the virus are detectable or symptoms are evident in the infected individual. For protection of patients who might otherwise receive HIV-1-infected body fluid (e.g., whole blood or plasma during transfusion), or products derived from blood or plasma, it is particularly important to detect the presence of the virus in the body fluid to prevent its use in such procedures or in products. It is also important that procedures and reagents used in detecting HIV-1 be able to detect relatively low numbers of viral copies which may be present in an infected individual.

Assays and reagents for detecting HIV-1 have been previously disclosed in, for example, U.S. Pat. Nos. 5,008,182, 5,594,122, 5,688,637 and 5,843,638; European Patent Nos. EP 178 978 B1, EP 181,150 B1 and EP 185,444 B1; published European Patent Application Nos. EP 403,333, EP 462,627 and EP 806,484; and PCT No. WO 99/61666.

The present invention includes oligonucleotide sequences used as primers for amplification and probes for detection of HIV-1 nucleic acid present in a biological sample, using an assay that preferably includes transcription-mediated nucleic acid amplification (e.g., as previously disclosed by Kacian et al., U.S. Pat. Nos. 5,399,491 and 5,554,516). The preferred detection method uses known homogeneous detection techniques to detect, in a mixture, a labeled probe that is bound to an amplified nucleic acid (as disclosed, for example, in Arnold et al. *Clin. Chem.* 35:1588-1594 (1989); Nelson et al., U.S. Pat. No. 5,658,737; and Lizardi et al., U.S. Pat. Nos. 5,118,801 and 5,312,728). The present invention also includes nucleic acid oligonucleotide sequences that are useful for capturing the HIV-1 target using nucleic acid hybridization techniques that preferably use magnetic particles in separation of the captured target (Whitehead et al., U.S. Pat. Nos. 4,554,088 and 4,695,392).

SUMMARY OF THE INVENTION

According to one aspect of the invention, there are provided oligomers comprising a base sequence of SEQ ID NO:1, SEQ ID NO:2, SEQ ID NO:3, SEQ ID NO:4, SEQ ID NO:5, SEQ ID NO:6, SEQ ID NO:10, SEQ ID NO:17, SEQ ID NO:18, SEQ ID NO:19, SEQ ID NO:20, SEQ ID NO:21, SEQ ID NO:42, SEQ ID NO:45, SEQ ID NO:46, SEQ ID NO:47, SEQ ID NO:50, SEQ ID NO:51, SEQ ID NO:52 or SEQ ID NO:57. One embodiment includes oligomers wherein the base sequence is that of SEQ ID NO:2, SEQ ID NO:4, SEQ ID NO:6, SEQ ID NO:10, SEQ ID NO:17, SEQ ID NO:18 or SEQ ID NO:45. Another embodiment includes oligomers further comprising a backbone that includes at least one 2'-methoxy RNA group, at least one 2' fluoro-substituted RNA group, at least one peptide nucleic acid linkage, at least one phosphorothioate linkage, at least one methylphosphonate linkage or any combination thereof. Another embodiment includes oligomers in which the base sequence comprises the sequence of SEQ ID NO:1, SEQ ID NO:2, SEQ ID NO:3, SEQ ID NO:4, SEQ ID NO:5, SEQ ID NO:6, SEQ ID NO:17, SEQ ID NO:18, SEQ ID NO:19, SEQ ID NO:20 or SEQ ID NO:45, and the backbone comprises at least one 2'-methoxy RNA group.

According to another aspect of the invention, there are oligomers consisting of a base sequence of SEQ ID NO:7, SEQ ID NO:8, SEQ ID NO:9, SEQ ID NO:11, SEQ ID NO:12, SEQ ID NO:13, SEQ ID NO:16, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:43, SEQ ID NO:44, SEQ ID NO:48, SEQ ID NO:49, SEQ ID NO:54, SEQ ID NO:55 or SEQ ID NO:56. In one embodiment, the oligomer has a base sequence of SEQ ID NO:8, SEQ ID NO:9, SEQ ID NO:11, SEQ ID NO:13 or SEQ ID NO:16. In another embodiment, the base sequence of the oligomer is joined by a backbone that includes at least one 2'-methoxy RNA group, at least one 2' fluoro-substituted RNA group, at least one peptide nucleic acid linkage, at least one phosphorothioate linkage, at least one methylphosphonate linkage or any combination thereof.

According to another aspect of the invention, there are provided labeled oligomers comprising a base sequence of SEQ ID NO:16, SEQ ID NO:17, SEQ ID NO:18, SEQ ID NO:39, SEQ ID NO:40, SEQ ID NO:41, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 or SEQ ID NO:56; and a detectable label joined directly or indirectly to the base sequence. In one embodiment, the detectable label is a luminescent compound. In another embodiment, the base sequence is joined by a backbone comprising at least one 2'-methoxy RNA group. One embodiment is a labeled oligomer having the base sequence of SEQ ID NO:16, SEQ ID NO:17 or SEQ ID NO:18, and the label that is a chemiluminescent compound. A preferred embodiment is a labeled oligomer having the base sequence of SEQ ID NO:16 containing an inosine at residue 7, and an acridinium ester compound as the label.

According to another aspect of the invention, there is provided a method of detecting HIV-1 RNA in a biological sample, comprising the steps of: providing a biological sample containing HIV-1 RNA; contacting the biological sample with at least one capture oligomer comprising a base sequence that hybridizes specifically to a target region in LTR or pol sequences of HIV-1 RNA, thus forming a capture oligomer:HIV-1 RNA complex; separating the capture oligomer:HIV-1 RNA complex from the biological sample; then amplifying the LTR or pol sequences, or a cDNA made therefrom, using a nucleic acid polymerase in vitro to produce an amplified product; and detecting the amplified product using a labeled detection probe that hybridizes specifically with the amplified product. In one embodiment, the contacting step uses a capture oligomer that further comprises a tail sequence that binds to a complementary sequence immobilized on a solid support. In another embodiment, the base sequence of the capture oligomer that hybridizes specifically to a target region in LTR or pol sequences comprises a sequence of SEQ ID NO:1, SEQ ID NO:3, SEQ ID NO:5, SEQ ID NO:19 or SEQ ID NO:57. In another embodiment, the capture oligomer comprises the base sequence of at least one of SEQ ID NO:2, SEQ ID NO:4, SEQ ID NO:6, SEQ ID NO:20 or SEQ ID NO:45, or is any combination of oligomers of SEQ ID NO:2, SEQ ID NO:4, SEQ ID NO:6, SEQ ID NO:20 or SEQ ID NO:45. In a preferred embodiment, the capture oligomer is any combination of at least two oligomers having base sequences selected from the group of SEQ ID NO:2, SEQ ID NO:4 and SEQ ID NO:6. In one embodiment, the capture oligomer is a combination of oligomers having base sequences of SEQ ID NO:20 and SEQ ID NO:6, or SEQ ID NO:45 and SEQ ID NO:6. In another embodiment, the amplifying step uses at least two amplification oligomers that bind specifically to LTR or pol sequences or complementary sequences thereof. Preferably, the amplifying step uses at least two amplification oligomers for amplifying LTR sequences selected from the group consisting of SEQ ID NO:7, SEQ ID NO:8, SEQ ID NO:9, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37 and SEQ ID NO:38. Another embodiment uses, in the amplifying step, at least two amplification oligomers for amplifying pol sequences selected from the group consisting of: SEQ ID NO:10, SEQ ID NO:11, SEQ ID NO:12, SEQ ID NO:13, SEQ ID NO:14, SEQ ID NO:15, SEQ ID NO:42, SEQ ID NO:43 and SEQ ID NO:44. In another embodiment, the amplifying step comprises a transcription-associated amplification method that includes at least one promoter-primer comprising a promoter sequence that is recognized by an RNA polymerase when the promoter sequence is double stranded, wherein the promoter sequence is covalently attached to the 5' end of a LTR-specific sequence selected from the group consisting of SEQ ID NO:7, SEQ ID NO:21, SEQ ID NO:23, SEQ ID NO:25, SEQ ID NO:27, SEQ ID NO:29, SEQ ID NO:31 and SEQ ID NO:33, or a pol-specific sequence selected from the group consisting of SEQ ID NO:12 and SEQ ID NO:14; and at least one primer comprising a LTR-specific sequence selected from the group consisting of SEQ ID NO:9, SEQ ID NO:35, SEQ ID NO:36, SEQ ID NO:37 and SEQ ID NO:38, or a pol-specific sequence selected from the group consisting of SEQ ID NO:10, SEQ ID NO:11 and SEQ ID NO:42, provided that at least one LTR-specific promoter-primer is combined with at least one LTR-specific primer for amplifying a LTR target region, or at least one pol-specific promoter-primer is combined with at least one pol-specific primer for amplifying a pol target region. In one embodiment, the amplifying step comprises a transcription-associated amplification method that includes at least one promoter-primer having a LTR-specific sequence selected from the group consisting of SEQ ID NO:8, SEQ ID NO:22, SEQ ID NO:24, SEQ ID NO:26, SEQ ID NO:28, SEQ ID NO:30, SEQ ID NO:32 and SEQ ID NO:34, or a pol-specific sequence selected from the group consisting of SEQ ID NO:13, SEQ ID NO:15, SEQ ID NO:43 and SEQ ID NO:44; and at least one primer having a LTR-specific sequence selected from the group consisting of SEQ ID NO:9, SEQ ID NO:35, SEQ ID NO:36, SEQ ID NO:37 and SEQ ID NO:38, or a pol-specific sequence selected from the group consisting of SEQ ID NO:10, SEQ ID NO:11 and SEQ ID NO:42, provided that at least one LTR-specific promoter-primer is combined with at least one LTR-specific primer for amplifying a LTR target region, or at least one pol-specific promoter-primer is combined with at least one pol-specific primer for amplifying a pol target region. Preferably, the amplifying step uses any of the following combinations of promoter-primers and primers: promoter-primers of SEQ ID NO:13 and SEQ ID NO:15, with primers of SEQ ID NO:10 and SEQ ID NO:11; promoter-primers of SEQ ID NO:13 and SEQ ID NO:15, with primers of SEQ ID NO:42 and SEQ ID NO:11; promoter-primers of SEQ ID NO:43 and SEQ ID NO:15, with primers of SEQ ID NO:10 and SEQ ID NO:11; promoter-primers of SEQ ID NO:13 and SEQ ID NO:44, with primers of SEQ ID NO:10 and SEQ ID NO:11; promoter-primers of SEQ ID NO:7, SEQ ID NO:13 and SEQ ID NO:15, with primers of SEQ ID NO:9, SEQ ID NO:10 and SEQ ID NO:11; a promoter-primer of SEQ ID NO:8, and a primer of SEQ ID NO:9; a promoter-primer of SEQ ID NO:8, and a primer of SEQ ID NO:35; a promoter-primer of SEQ ID NO:8, and a primer of SEQ ID NO:36; a promoter-primer of SEQ ID NO:30, and a primer of SEQ ID NO:9; a promoter-primer of SEQ ID NO:30, and a primer of SEQ ID NO:36; a promoter-primer of SEQ ID NO:32, and a primer of SEQ ID NO:9; a promoter-primer of SEQ ID NO:34, and a primer of SEQ ID NO:36; a promoter-primer of SEQ ID NO:13, and a primer of SEQ ID NO:10; or a promoter-primer of SEQ ID NO:7, and a primer of SEQ ID NO:9. In one embodiment, the detecting step uses at least one labeled detection probe having a base sequence selected from the LTR-specific group consisting of SEQ ID NO:16, SEQ ID NO:39, SEQ ID NO:40 and SEQ ID NO:41, or the pol-specific group consisting of SEQ ID NO:17, SEQ ID NO:18, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 and SEQ ID NO:56, or a combination thereof. In another embodiment, the detecting step uses a combination of at least two labeled detection probes having the base sequences of SEQ ID NO:16, SEQ ID NO:17 or SEQ ID NO:18. Preferably, the labeled detection probe of SEQ ID NO:16 has an inosine at position 7. One embodiment, in the detecting step, uses at least one labeled detection probe having a base sequence selected from the LTR-specific group consisting of SEQ ID NO:16, SEQ ID NO:39, SEQ ID NO:40 and SEQ ID NO:41. Another embodiment, in the detecting step, uses at least one labeled detection probe having a base sequence selected from the pol-specific group consisting of SEQ ID NO:17, SEQ ID NO:18, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 and SEQ ID NO:56. In one embodiment, the detecting step uses at least one labeled detection probe that includes at least one 2'-methoxy backbone linkage. Another embodiment includes the contacting step that uses capture oligomers having the sequences of SEQ ID NO:2, SEQ ID NO:4 and SEQ ID NO:6; the amplifying step that uses promoter-primers having the sequences of SEQ ID NO:8, SEQ ID NO:13 and SEQ ID NO:15 and primers having the sequences of SEQ ID NO:9, SEQ ID NO:10 and SEQ ID NO:11; and the detecting step that uses labeled detection probes having the sequences of SEQ ID NO:16, SEQ ID NO:17 and SEQ ID NO:18. In one embodiment, the contacting step uses at least two capture oligomers that hybridize to different sequences in the target region; the amplifying step uses at least two different promoter-primers that hybridize to a first set of sequences within the target region and at least two different primers that hybridize to a second set of sequences within the target region; and the detecting step uses at least two labeled probes that bind specifically to different sequences located between the first set and second set of sequences within the target region. In another embodiment, the contacting step uses capture oligomers having the sequences of SEQ ID NO:4 and SEQ ID NO:6; the amplifying step uses promoter-primers having the sequences of SEQ ID NO:13 and SEQ ID NO:15 and primers having the sequences of SEQ ID NO:10 and SEQ ID NO:11; and the detecting step uses labeled probes having the sequences of SEQ ID NO:17 and SEQ ID NO:18. In a preferred embodiment, the amplifying step uses at least two promoter-primers that hybridize to a first set of overlapping sequences within the target region, at least two primers that hybridize to a second set of overlapping sequences within the target region, or a combination thereof.

According to another aspect of the invention these is provided a kit comprising a plurality of oligomers having the sequences of SEQ ID NO:10, SEQ ID NO:11, SEQ ID NO:13, SEQ ID NO:15, SEQ ID NO:17 and SEQ ID NO:18, wherein the oligomers having the sequences of SEQ ID NO:17 and SEQ ID NO:18 are labeled with a detectable label. In one embodiment, the kit further includes oligomers having the sequences of SEQ ID NO:8, SEQ ID NO:9 and SEQ ID NO:16, wherein the oligomer of SEQ ID NO:16 is labeled with a detectable label.

Figure 1:
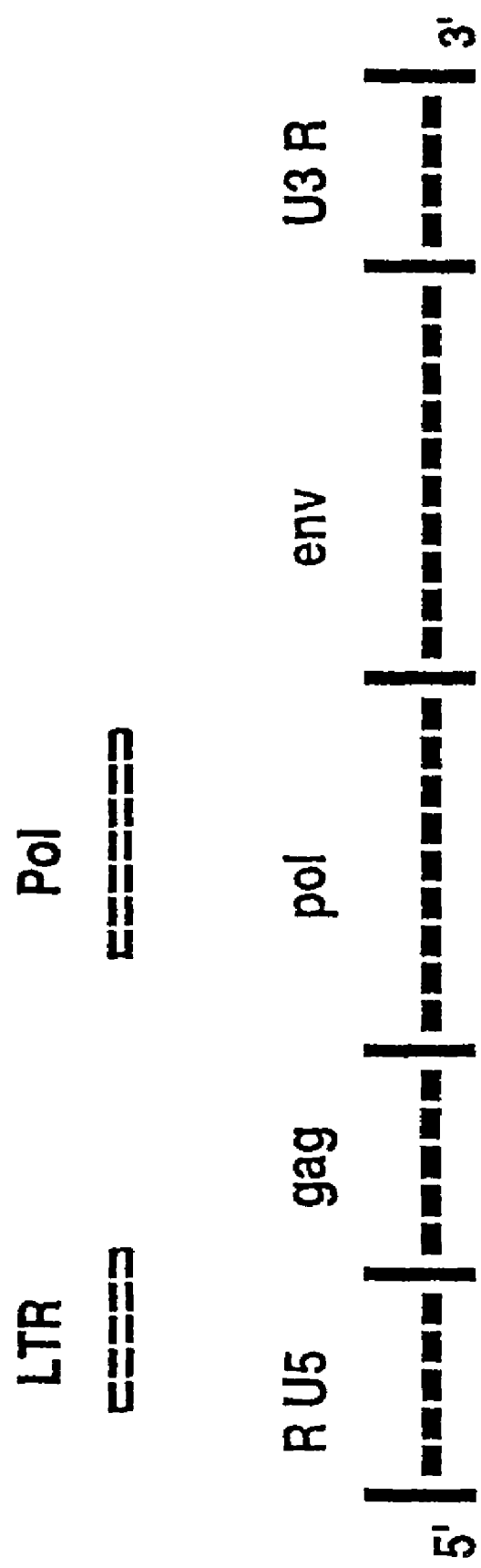
FIG. 1 is a schematic drawing of HIV-1 RNA (indicated in a 5' to 3' orientation by the thick dashed line divided into portions by vertical lines) showing the relative positions of genes ("gag", "pol", "env") and untranslated 5' and 3' regions ("R U5" and "U3 R" respectively) which contain long terminal repeats ("LTR"); target regions are indicated by the double-dashed lines labeled "LTR" and "Pol".

The accompanying drawings illustrate some embodiments of the invention. These drawings, together with the description, serve to explain and illustrate the principles of the invention.

DETAILED DESCRIPTION OF THE INVENTION

The present invention includes methods of detecting HIV-1 nucleic acids present in biological samples derived from humans, preferably in blood, serum or plasma. The present invention also includes compositions which include nucleic acid capture oligomers (or capture oligonucleotides) used to specifically capture HIV-1 target sequences present in a biological sample, nucleic acid amplification oligomers (or primers) used to specifically amplify selected HIV-1 nucleic acid sequences and nucleic acid probe oligomers (probes or labeled probes) for detecting amplified HIV-1 sequences.

The nucleic acid sequences of this invention are useful for capturing, amplifying and detecting HIV-1 nucleic acid present in a biological sample such human blood, serum, plasma or other body fluid containing HIV-1. The methods of the present invention are valuable for detecting HIV-1 nucleic acid in a biological sample, and thus are important for diagnosis of HIV-1 infection and for screening blood and blood products that may contain infectious virus, to prevent infecting individuals through transfusion with infected blood or plasma. Such screening is also important to prevent HIV-1 contamination in blood-derived therapeutics.

By "biological sample" is meant any tissue or material derived from a living or dead human which may contain the target HIV-1 nucleic acid, including, for example, peripheral blood or bone marrow, plasma, serum, cervical swab samples, biopsy tissue including lymph nodes, respiratory tissue or exudates, gastrointestinal tissue, urine, feces, semen or other body fluids, tissues or materials. The biological sample may be treated to physically or mechanically disrupt tissue or cell structure, thus releasing intracellular components into a solution which may contain enzymes, buffers, salts, detergents and the like which are used to prepare the biological sample using standard methods for analysis.

By "nucleic acid" is meant a multimeric compound comprising nucleosides or nucleoside analogs which have nitrogenous heterocyclic bases, or base analogs, where the nucleosides are linked together by phosphodiester bonds to form a polynucleotide. The term "nucleic acid" includes conventional RNA and DNA oligomers and those that include base analogs or substitutions. The "backbone" of a nucleic acid may be made up of a variety of known linkages, including one or more sugar-phosphodiester linkages, peptide-nucleic acid bonds (i.e., "peptide nucleic acids" as described by Hydig-Hielsen et al., PCT No. WO 95/32305), phosphorothioate linkages, methylphosphonate linkages or combinations thereof. Sugar moieties of the nucleic acid may be either ribose or deoxyribose, or similar compounds having known substitutions, such as, for example, 2' methoxy substitutions and 2' halide substitutions (e.g., 2'-F). The nitrogenous bases may be conventional bases (A, G, C, T, U), known analogs thereof (e.g., inosine; see *The Biochemistry of the Nucleic Acids* 5-36, Adams et al., ed., 11$^{th}$ ed., 1992), known derivatives of purine or pyrimidine bases (e.g., N$^4$-methyl deoxyguanosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-aminopyrimidines, 4-dimethylhydrazine-pyrimidines, and O$^4$-alkyl-pyrimidines; see, Cook, PCT No. WO 93/13121) and "abasic" residues where the backbone includes no nitrogenous base for one or more residues of the polymer (see Arnold et al., U.S. Pat. No. 5,585,481). A nucleic acid may comprise only conventional sugars, bases and linkages found in RNA and DNA, or may include both conventional components and substitutions (e.g., conventional bases linked via a methoxy backbone, or a nucleic acid including conventional bases and one or more base analogs).

The backbone composition of an oligomer may affect stability of a hybridization complex (e.g., formed by hybridization of a capture oligomer to a target nucleic acid). Preferred backbones include peptide linkages as in peptide nucleic acid, sugar-phosphodiester type linkages as in RNA and DNA, or derivatives thereof. Peptide nucleic acids are advantageous for forming a hybridization complex with RNA. In some embodiments, the backbone is made up of sugar-phosphodiester type linkages in which the sugar group and/or the linkage joining the groups is altered relative to standard DNA or RNA to enhance hybridization complex stability. For example, an oligomer having one or more 2'-methoxy substituted RNA groups or a 2'-fluoro substituted RNA forms a stable hybridization complex with a complementary 2' OH RNA. A linkage joining two sugar groups may affect hybridization complex stability by affecting the overall charge or the charge density, or by affecting steric association (e.g., steric interactions due to bulky linkages may reduce hybridization complex stability). Preferred embodiments include linkages with charged (e.g., phosphorothioates) or neutral (e.g., methylphosphonates) groups to affect complex stability.

By "oligonucleotide" or "oligomer" is meant a nucleic acid having generally less than 1,000 residues, including polymers falling in a size range having a lower limit of about 2 to 5 residues and an upper limit of about 500 to 900 residues. Preferably, oligomers of the present invention fall in a size range having a lower limit of about 5 to about 15 residues and an upper limit of about 50 to 600 residues. More preferably, oligomers of the present invention fall in a size range having a lower limit of about 10 to about 20 residues and an upper limit of about 22 to 100 residues. Oligomers may be purified from naturally occurring sources, but preferably are synthesized using any of a variety of well known enzymatic or chemical methods.

By "amplification oligonucleotide" or "amplification oligomer" is meant an oligonucleotide that hybridizes to a target nucleic acid, or its complement, and participates in a nucleic acid amplification reaction. Examples of amplification oligonucleotides include primers and promoter-primers. Preferably, an amplification oligonucleotide contains at least about 10 contiguous bases, and more preferably at least about 12 contiguous bases, which are complementary to a region of the target nucleic acid sequence (or a complementary strand thereof). The contiguous bases are preferably at least about 80%, more preferably at least about 90%, and most preferably greater than 95% complementary to a region to which the amplification oligonucleotide binds. An amplification oligonucleotide is preferably about 10 to about 60 bases long and optionally may include modified nucleotides or analogs.

Amplification oligonucleotides or oligomers also may be referred to as "primers" or "promoter-primers." A "primer" refers to an optionally modified oligonucleotide which is capable of hybridizing to a template nucleic acid and which has a 3' end that can be extended in a known polymerization reaction. The 5' region of the primer may be non-complementary to the target nucleic acid; if the 5' non-complementary region includes a promoter sequence, it may be referred to as a "promoter-primer." Those skilled in the art will appreciate that any oligomer that can function as a primer (i.e., an amplification oligonucleotide that hybridizes specifically to a target sequence and has a 3' end capable of being extended by a polymerase activity) can be modified to include a 5' promoter sequence, and thus could function as a promoter-primer. Similarly, any promoter-primer can be modified by removal of, or synthesis without, a promoter sequence and still function as a primer.

By "LTR-specific sequence" is meant any sequence of nucleic acid bases that hybridizes specifically to a sequence in an HIV-1 LTR region or its complement under standard hybridization conditions; an LTR-specific sequence may further contain or be covalently linked to nucleic acid bases that do not hybridize specifically to an LTR sequence or its complement, provided that such non-LTR-specific bases do not interfere with hybridization of the LTR-specific sequence to its target sequence. Similarly, by "Pol-specific sequence" is meant any sequence of nucleic acid bases that hybridizes specifically to a sequence in an HIV-1 pol region or its complement under standard hybridization conditions as described herein; a pol-specific sequence may further contain or be covalently linked to nucleic acid bases that do not hybridize specifically to a pol sequence or its complement, provided that such non-pol-specific bases do not interfere with hybridization of the pol-specific sequence to its target sequence.

By "amplification" is meant any known in vitro procedure for obtaining multiple copies of a target nucleic acid sequence or its complement or fragments thereof. Amplification of "fragments thereof" refers to production of an amplified nucleic acid containing less than the complete target region nucleic acid sequence or its complement. Such fragments may be produced by amplifying a portion of the target nucleic acid, for example, by using an amplification oligonucleotide which hybridizes to, and initiates polymerization from, an internal position of the target nucleic acid. Known amplification methods include, for example, transcription-mediated amplification, replicase-mediated amplification, polymerase chain reaction (PCR) amplification, ligase chain reaction (LCR) amplification and strand-displacement amplification (SDA). Replicase-mediated amplification uses self-replicating RNA molecules, and a replicase such as QB-replicase (e.g., see Kramer et al., U.S. Pat. No. 4,786,600; PCT No. WO 90/14439). PCR amplification is well known and uses a DNA polymerase, primers and thermal cycling to synthesize multiple copies of the two complementary strands of DNA (e.g., see U.S. Pat. Nos. 4,683,195, 4,683,202, and 4,800,159; *Methods in Enzymology*, 1987, Vol. 155: 335-350). LCR amplification uses at least four separate oligonucleotides to amplify a target and its complementary strand by using multiple cycles of hybridization, ligation, and denaturation (see EP Pat. App. No. 0 320 308). SDA is a method in which a primer contains a recognition site for a restriction endonuclease such that the endonuclease will nick one strand of a hemimodified DNA duplex that includes the target sequence, followed by amplification in a series of primer extension and strand displacement steps (see Walker et al., *Proc. Natl. Acad. Sci. USA* 89:392-396 (1992); and U.S. Pat. No. 5,422,252) Transcription-associated amplification is a preferred embodiment of the present invention. It will be apparent to one skilled in the art, however, that the amplification oligonucleotides disclosed herein are readily applicable to other amplification methods that use primer extension.

By "transcription-associated amplification" or "transcription-mediated amplification" is meant any type of nucleic acid amplification that uses an RNA polymerase to produce multiple RNA transcripts from a nucleic acid template. Transcription-associated amplification generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of transcription-associated amplification are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. The methods of Kacian et al. are used in preferred embodiments of the present invention.

By "probe" is meant a nucleic acid oligomer that hybridizes specifically to a target sequence in a nucleic acid, preferably in an amplified nucleic acid, under standard conditions that promote hybridization, thereby allowing detection of the target sequence or amplified nucleic acid. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). A probe's "target" generally refers to a sequence within (i.e., a subset of) an amplified nucleic acid sequence or target region which hybridizes specifically to at least a portion of a probe oligomer using standard hydrogen bonding (i.e., base pairing). A probe may comprise target-specific sequences and other sequences that contribute to three-dimensional conformation of the probe (e.g., as described in Lizardi et al., U.S. Pat. Nos. 5,118,801 and 5,312,728). Sequences that are "sufficiently complementary" allow stable hybridization of a probe oligomer to a target sequence even thought it is not completely complementary to the probe's target-specific sequence.

By "sufficiently complementary" is meant a contiguous nucleic acid base sequence that is capable of hybridizing to another base sequence by hydrogen bonding between a series of complementary bases. Complementary base sequences may be complementary at each position in the base sequence of an oligomer using standard base pairing or may contain one or more residues that are not complementary using standard hydrogen bonding (including abasic "nucleotides"), but in which the entire complementary base sequence is capable of specifically hybridizing with another base sequence in appropriate hybridization conditions. Contiguous bases are preferably at least about 80%, more preferably at least about 90%, and most preferably greater than 95% complementary to a sequence to which an oligomer is intended to specifically hybridize. To those skilled in the art, appropriate hybridization conditions are well known, can be predicted based on base composition, or can be determined empirically by using routine testing (e.g., see Sambrook et al., *Molecular Cloning,* *A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51 and 11.47-11.57 particularly at §§ 9.50-9.51, 11.12-11.13, 11.45-11.47 and 11.55-11.57).

By "capture oligonucleotide" or "capture oligomer" is meant at least one nucleic acid oligomer that provides means for specifically joining a target sequence and an immobilized oligomer due to base pair hybridization. A capture oligomer preferably includes two binding regions: a target sequence-binding region and an immobilized probe-binding region, usually contiguous on the same oligomer, although the capture oligomer may include a target sequence-binding region and an immobilized probe-binding region which are present on two different oligomers joined together by one or more linkers. For example, an immobilized probe-binding region may be present on a first oligomer, the target sequence-binding region may be present on a second oligomer, and the two different oligomers are joined by hydrogen bonding with a linker that is a third oligomer containing sequences that hybridize specifically to the sequences of the first and second oligomers. Sometimes, a capture oligomer is referred to as a "capture probe."

By "immobilized probe" or "immobilized nucleic acid" is meant a nucleic acid that joins, directly or indirectly, a capture oligomer to an immobilized support. An immobilized probe is an oligomer joined to a solid support that facilitates separation of bound target sequence from unbound material in a sample. Any known solid support may be used, such as matrices and particles free in solution, including for example, nitrocellulose, nylon, glass, polyacrylate, mixed polymers, polystyrene, silane polypropylene and metal particles, preferably, magnetically attractable particles. Preferred supports are monodisperse magnetic spheres (i.e., uniform in size±about 5%), thereby providing consistent results, to which an immobilized probe is joined directly (e.g., via covalent linkage, chelation, or ionic interaction), or indirectly (e.g., via one or more linkers), where the linkage or interaction is stable during nucleic acid hybridization conditions.

By "separating" or "purifying" is meant that one or more components of a biological sample are removed from one or more other components of the sample. Sample components include nucleic acids in a generally aqueous solution phase which may also include materials such as proteins, carbohydrates, lipids and labeled probes. Preferably, this step removes at least about 70%, more preferably at least about 90% and, most preferably, at least about 95% of the other sample components from the desired component.

By "label" or "detectable label" is meant a molecular moiety or compound that can be detected or can lead to a detectable response. A label is joined, directly or indirectly, to a nucleic acid probe. Direct labeling can occur through bonds or interactions that link the label to the probe, including covalent bonds or non-covalent interactions (e.g., hydrogen bonding, hydrophobic and ionic interactions) or through formation of chelates or coordination complexes. Indirect labeling can occur through use of a bridging moiety or "linker", such as an antibody or additional oligonucleotide(s), which is either directly or indirectly labeled, and which can amplify a detectable signal. A label can be any known detectable moiety, such as, for example, a radionuclide, ligand (e.g., biotin, avidin), enzyme or enzyme substrate, reactive group, chromophore, such as a dye or particle that imparts a detectable color (e.g., latex or metal particles), luminescent compond (e.g., bioluminescent, phosphorescent or chemiluminescent labels) and fluorescent compound.

Preferably, the label on a labeled probe that is detectable in a homogeneous assay system, i.e., where, in a mixture, bound labeled probe exhibits a detectable change, such as stability or differential degradation, compared to unbound labeled probe, without physically removing hybridized from unhybridized forms of the label or labeled probe. A "homogeneous detectable label" refers to a label whose presence can be detected in a homogeneous fashion as previously described in detail in Arnold et al., U.S. Pat. No. 5,283,174; Woodhead et al., U.S. Pat. No. 5,656,207; and Nelson et al., U.S. Pat. No. 5,658,737. Preferred labels for use in a homogenous assay include chemiluminescent compounds (e.g., see Woodhead et al., U.S. Pat. No. 5,656,207; Nelson et al., U.S. Pat. No. 5,658, 737; and Arnold, Jr., et al., U.S. Pat. No. 5,639,604). Preferred chemiluminescent labels are acridinium ester ("AE") compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE, 1- or 3-methyl-meta-difluoro-AE, and 2-methyl-AE). Synthesis and methods of attaching labels to nucleic acids and detecting labels are well known in the art (e.g., see Sambrook et al., *Molecular Cloning, A Laboratory Manual*, 2nd ed. (Cold Spring Harbor Laboratory Press, Cold Spring Habor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333; and Becker et al., European Pat. App. No. 0 747 706).

By "consisting essentially of" is meant that additional component(s), composition(s) or method step(s) that do not materially change the basic and novel characteristics of the present invention may be included in the compositions or kits or methods of the present invention. Such characteristics include the ability to detect HIV-1 nucleic acid in a biological sample such as whole blood or plasma, at a copy number of about 100 copies of HIV-1. Any component(s), composition (s), or method step(s) that have a material effect on the basic and novel characteristics of the present invention fall outside of this term.

Unless defined otherwise, all scientific and technical terms used herein have the same meaning as commonly understood by those skilled in the relevant art. General definitions of many of the terms used herein are provided, for example, in *Dictionary of Microbiology and Molecular Biology*, 2nd ed. (Singleton et al., 1994, John Wiley & Sons, New York, N.Y.) or *The Harper Collins Dictionary of Biology* (Hale & Marham, 1991, Harper Perennial, New York, N.Y.). Unless mentioned otherwise, the techniques employed or contemplated herein are standard methodologies well known to one of ordinary skill in the art. Examples are included to illustrate some embodiments of the invention.

The present invention includes compositions (nucleic acid capture oligomers, amplification oligomers and probes) and methods for detecting HIV-1 nucleic acid in a human biological sample. To design oligomer sequences appropriate for such uses, known HIV-1 DNA sequences, including subtypes, partial sequences, or complementary sequences, available from publicly accessible databases (e.g., GenBank) were aligned by matching regions of the same or similar sequences and compared using well known molecular biology techniques. The sequences used in the comparisons included (using their database designations): HIV3ALTRc, HIVANT70, HIVANT70C, HIVBAL1, HIVBaLTRc, HIVBbLTRc, HIVBRUCG, HIVCAM1, HIVCDC41, HIVD31, HIVEaLTRc, HIV1EbLTRc, HIVELI, HIVELICG, HIVHAN, HIVHXB2, HIVH9NL43, HIVJ233, HIVJRCSF, HIVJRFL, HIVJH31, HIVKEBO, HIVLAI, HIVMAL, HIVMCK1, HIVMN, HIVMNCG, HIVMVP5180, HIVNDK, HIVNL43, HIVNY5, HIVNY5CG, HIVOYI, HIVRF, HIVSC, HIVSF162, HIVSF2, HIV-subC, HIVU455, HIVTH475A, HIVYU2, HIVZ2Z6, HIV1SG3X, HIV1U12055, HIV1U21135, HIV1U23487, HIV1U26546, HIV1U26942, HIV1U34603, HIV1U34604, HIV1U39362, HIV1U3RA, HIV2ALTRc, HIV2BLTRc, HIV2CLTRc, HIV2132, HIV3BLTRc, HIV4ALTRc, HIV4BLTRc, HIV4CLTRc, and REHTLV3. The regions of the HIV-1 genome targeted for detection using the designed capture oligomers, primers and probes were the LTR and pol regions as shown schematically in FIG. 1. Although sequence comparisons may be facilitated by use of algorithms, those skilled in the art can readily perform such comparisons manually. Portions of sequences containing relatively few sequence variants between the compared sequences were chosen as a basis for designing synthetic oligomers suitable for use in capture, amplification and detection of amplified sequences. Other considerations in designing oligomers included the relative GC content of the sequence (ranging from about 30% to about 55%) and the relative absence of predicted secondary structure (e.g., hairpin turns forming intramolecular hybrids) within a sequence, using methods well known in the art.

Based on these analyses, the capture oligomer, amplification oligomers and probe sequences of SEQ ID NO:1 to SEQ ID NO:45 were designed. Generally, for capture oligomer sequences, the sequence that specifically binds to HIV-1 sequence is shown without a 3' tail (SEQ ID NO:1, 3, 5, and 19), and with a 3' tail sequence (SEQ ID NO:2, 4, 6, and 20). Generally, for sequences of T7 promoter primers, which include a T7 promoter sequence, the primer sequences are shown without the T7 promoter sequence (SEQ ID NO:7, 12, 14, 21, 23, 25, 27, 29, 31, and 33) and with a 5' T7 promoter sequence (SEQ ID NO:8, 13, 15, 22, 24, 26, 28, 30, 32, and 34). Although some T7 promoter primer sequences are shown only with a T7 promoter sequence (SEQ ID NO:43 and SEQ ID NO:44), those skilled in the art will appreciate that the primer sequence specific for HIV-1, with or without the T7 promoter sequence, may be useful as a primer under some amplification conditions.

Preferred capture oligomers include a sequence that binds specifically to an HIV-1 sequence in the LTR region or pol region (i.e., an HIV-1-binding sequence) which is covalently attached to a tail sequence. Any backbone to link the base sequence of a capture oligomer may be used, and in preferred embodiments the capture oligomer includes at least one methoxy linkage in the backbone. The tail sequence, which is preferably at the 3' end of a capture oligomer, is used to hybridize to a complementary base sequence to provide a means of capturing the hybridized target HIV-1 nucleic acid from the other components in the biological sample. Any base sequence that hybridizes to a complementary base sequence may be used in a tail sequence, which preferably has a sequence length of about 5 to 50 nucleotide residues. Preferred tail sequences are substantially homopolymeric, containing about 10 to about 40 nucleotide residues. For example, a tail may comprise about $(A)_{10}$ to about $(A)_{40}$ residues. Preferably, the tail of a capture oligomer includes about 14 to about 30 residues and is substantially homopolymeric in sequence. Preferred tail sequences include sequences of $TTT(A)_{14}$ to $TTT(A)_{30}$ and $(A)_{14}$ to $(A)_{30}$.

Figure 2:
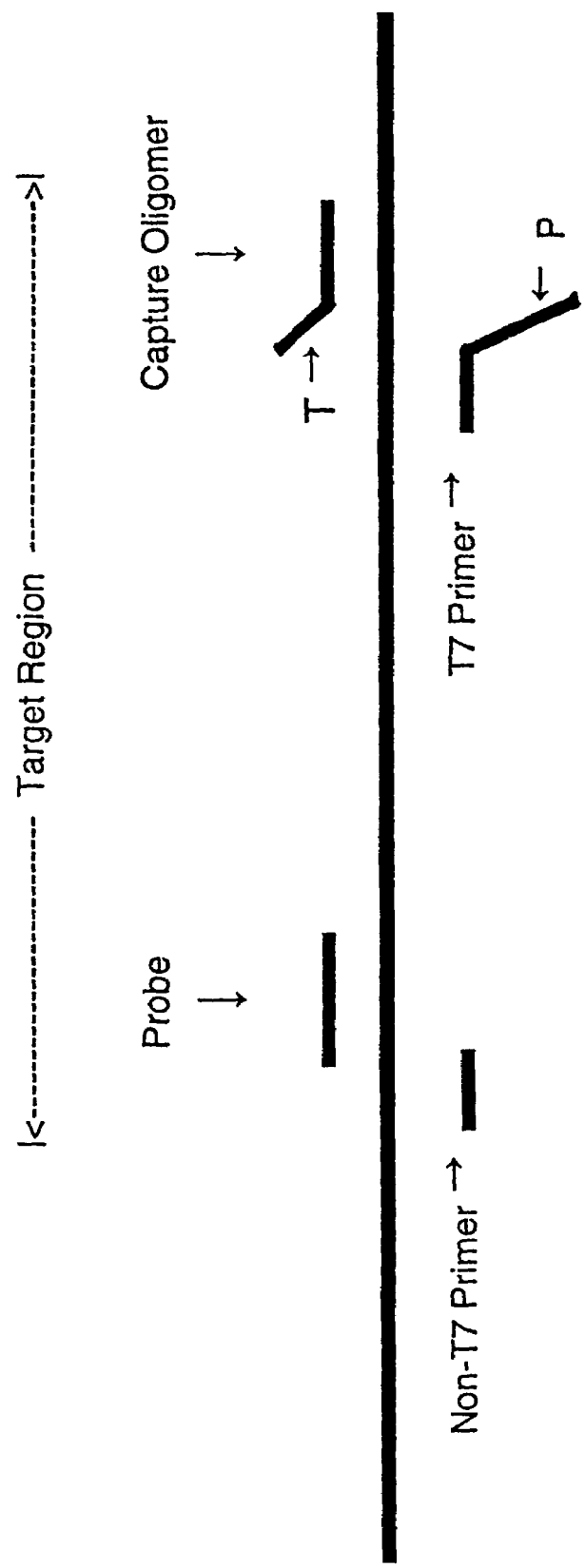
FIG. 2 is a schematic drawing of the components of an embodiment of the present invention for detecting a "Target Region" of HIV-1 nucleic acid (represented by the thick vertical line), where the positions of the following nucleic acids are shown relative to the target region: a "Capture Oligomer" refers to the nucleic acid used to hybridize to and capture the target nucleic acid prior to transcription-mediated amplification, where "T" refers to a 3' tail sequence used to hybridize to an immobilized oligomer having a complementary sequence (not shown); "Non-T7 Primer" and "T7 Primer" represent two amplification oligonucleotides used in transcription-mediated amplification where "P" indicates the promoter sequence of the T7 primer; and "Probe" refers to a labeled probe used to detect the amplified nucleic acid.

Preferred methods of the present invention are described and are illustrated by the examples. FIG. 2 illustrates one system for detecting a target region (i.e., a selected portion) of the HIV-1 genome (shown by the thick solid horizontal line). This system includes four oligomers (shown by the shorter solid lines): one capture oligomer which includes a sequence that hybridizes specifically to an HIV-1 sequence in the target region and a tail ("T") that hybridizes to complementary sequence immobilized on a solid support to capture the target region present in a biological sample; one T7 primer which includes a sequence that hybridizes specifically to an HIV-1 sequence in the target region and a T7 promoter sequence ("P") which, when double-stranded, serves as a functional promoter for T7 RNA polymerase; one non-T7 primer which includes a sequence that hybridizes specifically to a first strand cDNA made from the target region sequence using the T7 primer; and one labeled probe which includes a sequence that hybridizes specifically to a portion of the target region that has been amplified using the two primers.

Using the components illustrated in FIG. 2, an assay to detect HIV-1 sequences in a biological sample includes the steps of capturing the target nucleic acid using the capture oligomer, amplifying the captured target region using at least two primers, preferably by using a transcription-associated amplification reaction, and detecting the amplified nucleic acid by hybridizing the labeled probe to a sequence contained in the amplified nucleic acid and detecting a signal resulting from the bound labeled probe.

The capturing step preferably uses a capture oligomer as illustrated in FIG. 2, where under hybridizing conditions one portion of the capture oligomer specifically hybridizes to a sequence in the target nucleic acid and a tail portion serves as one portion of a binding pair, such as a ligand (e.g., a biotin-avidin binding pair) that allows the target region to be separated from other components of the sample. Preferably, the tail portion of the capture oligomer is a sequence that hybridizes to a complementary sequence that is immobilized by being bound to a solid support particle. Preferably, first, the capture oligomer and the target nucleic acid are in solution to utilize solution phase hybridization kinetics. Hybridization produces a capture oligomer:target nucleic acid complex which can be bound to an immobilized probe by hybridization of the tail portion of the capture oligomer with a complementary immobilized sequence. Thus, a complex comprising a target nucleic acid, capture oligomer and immobilized probe is formed under hybridization conditions. Preferably, the immobilized probe is a repetitious sequence, and more preferably a homopolymeric sequence (e.g., poly-A, poly-T, poly-C or poly-G), which is complementary to the tail sequence and attached to a solid support. For example, if the tail portion of the capture oligomer contains a poly-A sequence, then the immobilized probe would contain a poly-T sequence, although any combination of complementary sequences may be used. The capture oligomer may also contain "spacer" residues, which are one or more bases located between the base sequence that hybridizes to the target and the base sequence of the tail that hybridizes to the immobilized probe. For example, a tail portion consisting of TTT $(A)_{16}$ that hybridizes to a poly-dT immobilized probe contains a spacer consisting of TTT separating the base sequence that hybridizes to the target sequence and the $(A)_{16}$ sequence that hybridizes to the immobilized probe. Any solid support may be used such as matrices and particles free in solution (e.g., nitrocellulose, nylon, glass, polyacrylate, mixed polymers, polystyrene, silane polypropylene and, preferably, magnetically attractable particles). Methods of attaching an immobilized probe to the solid support are well known. The support is preferably a particle which can be retrieved from solution using standard methods (e.g., centrifugation, magnetic attraction of magnetic particles, and the like). Preferred supports are paramagnetic monodisperse particles (i.e., uniform in size±about 5%).

Retrieving the target nucleic acid:capture oligomer:immobilized probe complex concentrates the target nucleic acid (relative to its concentration in the biological sample) and purifies the target nucleic acid from amplification inhibitors which may be present in the biological sample. The captured target nucleic acid may be washed one or more times, further purifying the target (e.g., by resuspending the particles with the attached target nucleic acid:capture oligomer:immobilized probe complex in a washing solution and then retrieving the particles with the attached complex from the washing solution as described above). In a preferred embodiment, the capturing step takes place by sequentially hybridizing the capture oligomer with the target nucleic acid and then adjusting the hybridization conditions to allow hybridization of the tail portion of the capture oligomer with an immobilized complementary sequence (e.g., described in PCT No. WO 98/50583). When the capturing step, and any optional washing steps included in it, have been completed, the target nucleic acid is amplified, preferably without releasing it from the capture oligomer.

Amplifying the captured target region using the two primers can be accomplished using a variety of known nucleic acid amplification reactions, but preferably uses a transcription-associated amplification reaction. In such an embodiment, many strands of nucleic acid are produced from a single copy of target nucleic acid, thus permitting detection of the target by using detectable probes bound to the amplified sequences. Transcription-associated amplification has been described in detail elsewhere (Kacian et al., U.S. Pat. Nos. 5,399,491 and 5,554,516) and described briefly below. Preferably, transcription-associated amplification uses two types of primers (one referred to as a promoter-primer because it contains a promoter sequence, labeled "P" in FIG. 2, for an RNA polymerase), enzymes (a reverse transcriptase and an RNA polymerase), and substrates (deoxyribonucleoside triphosphates, ribonucleoside triphosphates) with appropriate salts and buffers in solution to produce multiple RNA transcripts from a nucleic acid template. Briefly, in the first step, a promoter-primer hybridizes specifically to a target sequence and reverse transcriptase creates a first strand cDNA by extension from the 3' end of the promoter-primer. The cDNA becomes available for hybridization with the second primer by using well known techniques, such as, by denaturing the duplex or using RNase H activity, which is preferably supplied by the reverse transcriptase, to degrade the RNA in a DNA:RNA duplex. A second primer then binds to the cDNA and a new strand of DNA is synthesized from the end of the second primer using reverse transcriptase, to create a double-stranded DNA having a functional promoter sequence at one end. RNA polymerase binds to the double-stranded promoter sequence and transcription produces multiple transcripts or "amplicons." These amplicons then are used in the transcription-associated amplification process, each serving as a template for a new round of replication as described above, thus generating large amounts of single-stranded amplified nucleic acid (about 100 to about 3,000 RNA transcripts synthesized from a single template). Preferably, amplification uses substantially constant reaction conditions (e.g., a single temperature).

A promoter-primer oligonucleotide contains a 5' sequence promoter sequence that, when double-stranded, serves as a functional promoter for an RNA polymerase, and a 3' sequence region that hybridizes specifically to a sequence in the target region. A preferred promoter-primer includes a promoter sequence specific for a T7 RNA polymerase, and such a promoter-primer may be referred to as a "T7 primer."

The second primer that does not include a promoter sequence is often referred to as a "non-T7 primer" to distinguish it from the T7 primer.

Referring to FIG. 2, during transcription-mediated amplification, the captured target nucleic acid is hybridized to a first primer shown as a T7 primer. Using reverse transcriptase, cDNA is synthesized from the T7 primer using the target RNA as the template. The second primer, shown as a non-T7 primer, hybridizes to the cDNA strand and reverse transcriptase forms a DNA duplex, thus forming a double-stranded functional T7 promoter. Then, T7 RNA polymerase generates multiple RNA transcripts by using the functional T7 promoter. By repeating these hybridization and polymerization steps following the initial cDNA synthesis step, additional RNA transcripts are produced thus amplifying target region-specific nucleic acid sequences.

The detecting step uses at least one labeled probe that binds specifically to the amplified nucleic acid (e.g., the RNA transcripts or amplicons resulting from transcription-mediated amplification). Preferably, the probe is labeled with a detectable label that produces a signal that can be detected without purifying the bound probe from unbound probe (i.e., a homogeneous detection system). More preferably, the probe is labeled with an acridinium ester compound from which a chemiluminescent signal is produced and detected, as described in detail previously (Arnold et al., U.S. Pat. No. 5,283,174 and U.S. Pat. No. 5,656,744; Nelson et al., U.S. Pat. No. 5,658,737).

Figure 3:
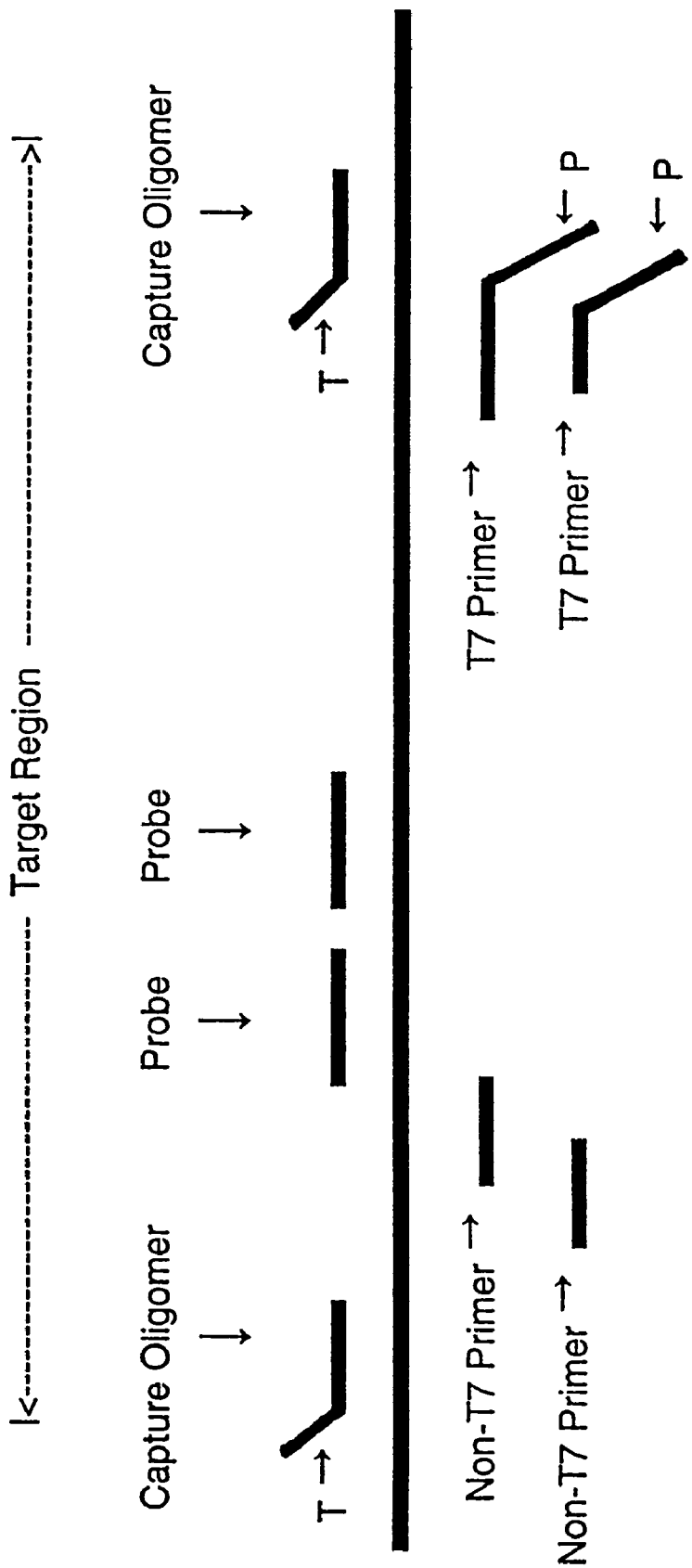
FIG. 3 is a schematic drawing, labeled as in FIG. 2, of the components of another embodiment of the present invention for detecting a HIV-1 nucleic acid Target Region using two capture oligomers, two non-T7 primers, two T7 primers and two labeled probes.

As illustrated in FIG. 3, transcription-associated amplification reactions may use multiple promoter-primers and primers for a target region. Referring to FIG. 3, two capture oligomers are used to capture target region nucleic acids. Then, during transcription-associated amplification, multiple T7 primers and non-T7 primers are used as described above. During the detection step, multiple labeled probes that bind specifically to the transcripts are used to detect the amplicons. For the purposes of illustration, FIG. 3 shows two different forms of each of the above components, although more than two of each component may be used in an assay reaction.

FIG. 3 illustrates two different capture oligomers used in the capture step, each hybridizing specifically to a different sequence of the target region. Preferably, one capture oligomer hybridizes to a 5' portion and a second capture oligomer hybridizes to a 3' portion of the target region. In embodiments which use multiple capture oligomers in the capture step, preferably both capture oligomers have substantially the same tail sequence to allow hybridization of both capture oligomers to the same immobilized probe species as described above. For example, the tail of two different capture oligomers may be poly-T sequences and the immobilized sequences are then complementary poly-A oligomers.

Referring to FIG. 3, following target capture, a portion of the target region is amplified, preferably using a transcription-associated amplification method that employs at least two T7 primers and at least two non-T7 primers. Although only two primers are needed for transcription-associated amplification (a T7 promoter primer and a non-T7 primer), the use of two or more different primers of each type has been found to enhance amplification of some target sequences. Surprisingly, even if two primers bind specifically to target sequences that overlap (as illustrated in FIG. 3), enhanced amplification was observed. That is, by providing primers that specifically bind to overlapping target sequences, enhanced amplification of the target region was observed, rather than inhibited amplification as might be expected, for example, if the primers compete for hybridization to the target sequence. An additional unexpected benefit was that, for some targets (e.g., HIV-1 Group O pol), the combination of at least two amplification oligomers that bind to overlapping target sequences allowed more efficient amplification of the target than was achieved using a system as illustrated in FIG. 2, which uses one primer and one promoter-primer.

Again referring to FIG. 3, following amplification of the target sequences, two or more different labeled probes that specifically hybridize to amplified sequences are used in the detecting step of the assay. As discussed above, any detectable label may be used and different labels may be used for the different probes. For example, one probe may be radiolabled another probe fluorescently labeled, thus providing different distinguishable signals. Preferably, the two or more labeled probes are each labeled with a label that allows for signal detection in a homogeneous system where unbound probe is distinguished from bound probe without requiring physical separation. In a preferred embodiment, the two or more labeled probes are labeled with a luminescent label, and more preferably the luminescent label is an AE compound that is detected as a chemiluminescent signal in a homogenous detection assay using well known procedures.

Although FIG. 2 illustrates an embodiment in which one of each component is used and FIG. 3 illustrates an embodiment in which two of each components is used, those skilled in the art will appreciate that different variations that combine features as illustrated in FIGS. 2 and 3 may be used. For example, an assay may use one capture oligomer to capture the target region, then may use two promoter-primers and two second primers during amplification, and finally may detect amplified products using one probe that binds specifically to all amplicons. In another example, multiple capture oligomers may be used to capture a target region nucleic acid, followed by transcription-mediated amplification using multiple promoter-primers but a single second primer sequence, followed by detection using one labeled probe. That is, different combinations of components of the basic assay shown in FIG. 2 may be used, so long as at least one of each component is present in the assay.

Figure 4A:
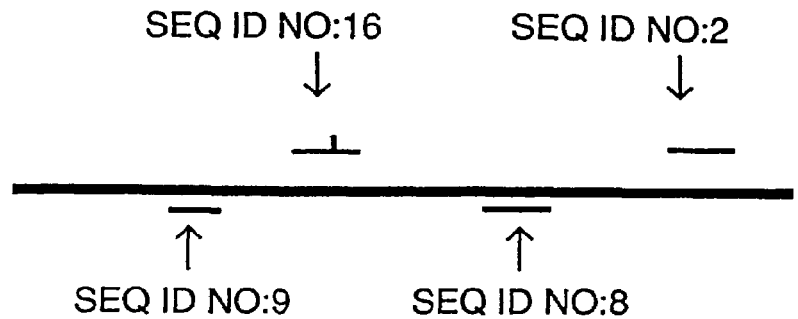
FIG. 4A is a schematic drawing of a preferred embodiment, as illustrated generically in FIG. 2, for detecting an HIV-1 LTR target region in which the capture oligomer is represented by SEQ ID NO:2, the non-T7 primer is represented by SEQ ID NO:9, the T7 primer is represented by SEQ ID NO:8, and the labeled probe is represented by SEQ ID NO:16.
Figure 4B:
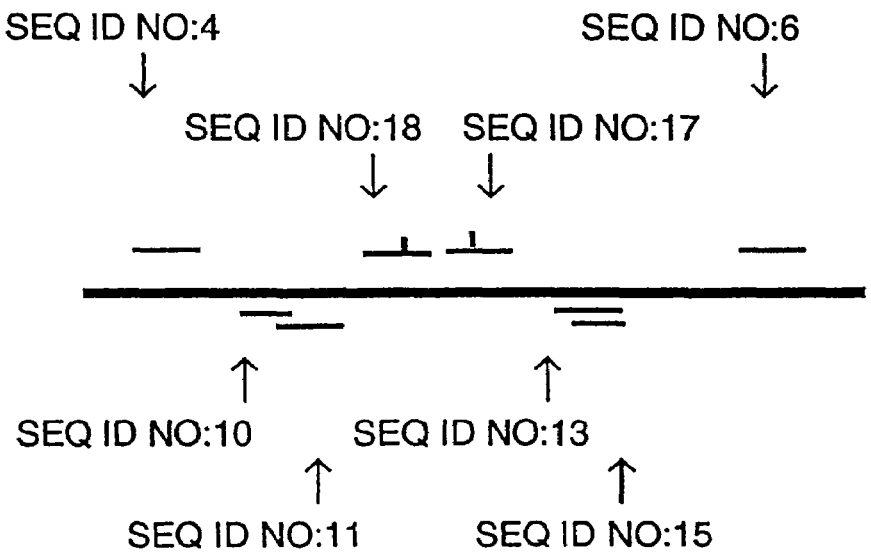
FIG. 4B is a schematic drawing of a preferred embodiment, as illustrated generically in FIG. 3, for detecting an HIV-1 pol target region in which the capture oligomers are represented by SEQ ID NO:4 and SEQ ID NO:6, the non-T7 primers are represented by SEQ ID NO:10 and SEQ ID NO:11, the T7 primers are represented by SEQ ID NO:13 and SEQ ID NO:15, and the labeled probes are represented by SEQ ID NO:17 and SEQ ID NO:18.

Examples of specific embodiments for detecting target regions in the HIV-1 LTR and pol sequences are illustrated in FIGS. 4A and 4B. As shown in FIG. 4A, for detecting HIV-1 LTR sequences, the capture oligomer includes the sequence of SEQ ID NO:2, the non-T7 primer includes the sequence of SEQ ID NO:9, the T7 primer includes the sequence of SEQ ID NO:8, and the labeled probe includes the sequence of SEQ ID NO:16, where the relative positions of these sequences are illustrated by the short horizontal lines above and below the long vertical line representing the LTR target region. Preferably, the labeled probe includes an AE-derived label as shown by the short vertical line joined to the horizontal line labeled SEQ ID NO:16. As shown in FIG. 4B, for detecting HIV-1 pol sequences, two of each type of oligomer are included in the assay, where the relative positions of these sequences are illustrated by the short horizontal lines above and below the long vertical line representing the pol target region. That is, two capture oligomers are used, the first having the sequence of SEQ ID NO:4 and the second having the sequence of SEQ ID NO:6; two non-T7 primers are used, the first having the sequence of SEQ ID NO:10 and the second having the sequence of SEQ ID NO:11; two T7 primers are used, the first having the sequence of SEQ ID NO:13 and the second having the sequence of SEQ ID NO:15; and two labeled probes are used, the first including the sequence of SEQ ID NO:17 and the second including the sequence of SEQ ID NO:18. Preferably, the labeled probe includes an AE-derived label as shown by the short vertical lines joined to the horizontal lines labeled SEQ ID NO:17 and SEQ ID NO:18.

For the methods described above, capture oligomers, amplification oligomers and labeled probes having specific sequences have been identified as useful for detecting HIV-1 target sequences that are localized to the LTR and pol regions of the HIV-1 genome. These specific sequences may include contiguous nucleic acid bases as occur in naturally occurring nucleic acids (A, T, G or C), analogs (e.g., inosine) or synthetic purine and pyrimidine derivatives, such as, e.g., P or K bases (Lin & Brown, 1989, *Nucl. Acids Res.* 17:10373-83; Lin & Brown, 1992, *Nucl. Acids Res.* 20: 5149-52), or combinations thereof in a single contiguous sequence. Preferred capture oligomers for the LTR target region include the HIV-1-binding sequences of SEQ ID NO:1 and SEQ ID NO:19, which are attached to any moiety that can serve as a binding partner (i.e., ligands) for linking the target region sequences to a retrievable solid phase. Preferably, the ligand is a 3' tail sequence that hybridizes to an immobilized complementary oligomer. Preferred LTR-specific capture oligomers that include a tail sequence are shown by the sequences of SEQ ID NO:2, SEQ ID NO:20 and SEQ ID NO:45. Preferred capture oligomers for the pol target region include the HIV-1-binding sequences of SEQ ID NO:3 and SEQ ID NO:5, attached to a tail sequence that hybridizes to an immobilized complementary oligomer.

Preferred capture oligomers for the pol target region that include tail sequences include the sequences of SEQ ID NO:4 and SEQ ID NO:6.

Preferred amplification oligomer sequences for amplifying sequences in the LTR region include SEQ ID NO:7, SEQ ID NO:8, SEQ ID NO:9, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37 and SEQ ID NO:38. Primer sequences for amplification of HIV-1 LTR sequences that are preferred T7 promoter primers include SEQ ID NO:8, SEQ ID NO:22, SEQ ID NO:24, SEQ ID NO:26, SEQ ID NO:28, SEQ ID NO:30, SEQ ID NO:32 and SEQ ID NO:34. Preferred non-T7 primer sequences for amplification of HIV-1 LTR sequences include SEQ ID NO:9, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:36, SEQ ID NO:37 and SEQ ID NO:38. Preferred combinations of primers for amplifying the HIV-1 LTR region in a transcription-mediated amplification reaction include at least one T7 promoter primer that includes the sequence of SEQ ID NO:8, SEQ ID NO:22, SEQ ID NO:24, SEQ ID NO:26, SEQ ID NO:28, SEQ ID NO:30, SEQ ID NO:32 or SEQ ID NO:34; and at least one non-T7 primer that includes the sequence of SEQ ID NO:9, SEQ ID NO:35, SEQ ID NO:36, SEQ ID NO:37 or SEQ ID NO:38.

Preferred amplification oligomer sequences for amplifying sequences in the pol region include SEQ ID NO:10, SEQ ID NO:11, SEQ ID NO:12, SEQ ID NO:13, SEQ ID NO:14, SEQ ID NO:15, SEQ ID NO:42, SEQ ID NO:43 and SEQ ID NO:44. Primer sequences for amplification of HIV-1 pol sequences that are preferred T7 promoter primers include SEQ ID NO:13, SEQ ID NO:15, SEQ ID NO:43 and SEQ ID NO:44. Preferred non-T7 primer sequences for amplification of HIV-1 pol target sequences include SEQ ID NO:10, SEQ ID NO:11, and SEQ ID NO:42. Preferred combinations of primers for amplifying the HIV-1 pol target region in a transcription-mediated amplification method include at least one T7 promoter primer that includes the sequence of SEQ ID NO:13, SEQ ID NO:15, SEQ ID NO:43 or SEQ ID NO:44; and at least one non-T7 primer that includes the sequence of SEQ ID NO:10, SEQ ID NO:11 or SEQ ID NO:42.

Preferred probes for hybridizing to amplified HIV-1 LTR sequences to provide detectable signals include the sequences of: SEQ ID NO:16, wherein the "N" residue may be any base (A, T, G, C) or inosine or analogs thereof (e.g., 5-nitro-indole or a 2'-methoxy base), and preferably is inosine; SEQ ID NO:39, wherein the "N" residues may be any base or inosine or analogs thereof; SEQ ID NO:40, wherein the "R" residue may be either A or G, and preferably is A; and SEQ ID NO:41. In one embodiment, the labeled probe sequence for detecting amplified LTR sequences has a methoxy backbone or at least one methoxy linkage in the nucleic acid backbone. Preferably the label in a labeled probe is a chemiluminescent AE compound (e.g., 2-methyl-AE) which is attached to the probe sequence via a linker substantially as described in Arnold et al., U.S. Pat. No. 5,585,481; and Arnold et al., U.S. Pat. No. 5,639,604, particularly as described at column 10, line 6 to column 11, line 3, and in Example 8. That is, preferred labeling positions are a central region of the probe and near a region of A/T base pairs, at a 3' or 5' terminus of the probe, or at or near a mismatch site with a known sequence that is not the desired target sequence. For example, using a probe having the sequence of SEQ ID NO:17, an AE label is preferably attached to a 3' or 5' terminus or at positions between adjacent residues from residues 5 to 14 or from residues 16 to 19, such as, for examples, between residues 6 and 7, or between residues 7 and 8, or between residues 10 and 11.

Individual embodiments of probes having the sequences of SEQ ID NO:16, SEQ ID NO:39, SEQ ID NO:40 and SEQ ID NO:41 were tested for binding to HIV-1 LTR sequences of subtype B, subtype G (having a base substitution in the LTR relative to subtype B) and Group O. For example, when a probe having SEQ ID NO:16 includes inosine at position 7, the $T_m$ for both subtype B and Group O were essentially the same (72-73° C.) and was higher for subtype G (about 80° C.), whereas when 5-nitro-indole was used at position 7, the $T_m$ for all three tested strains was about the same (70-73° C.). Similar tests were performed using the different embodiments of SEQ ID NO:39, and from all of the tests the following conclusions were drawn: substitution of one 2'-methoxyribose base for a deoxyribose base generally lowered the $T_m$ about 2° C.; inosine substituted for a base complementary to a residue that varied between target sequences aided hybridization to the target; and substitution of 5-nitro-indole for a base may increase hybridization kinetics.

Preferred probes for hybridizing to amplified HIV-1 pol target sequences to provide detectable signals include the sequences of SEQ ID NO:17, SEQ ID NO:18, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 and SEQ ID NO:56, and more preferably include SEQ ID NO:17 and SEQ ID NO:18. In one embodiment, the labeled probe sequence for detecting amplified HIV-1 pol sequences has a methoxy backbone. A preferred label is a chemiluminescent AE label, more preferably 2-methyl-AE, which is attached to the probe sequence substantially as described above.

The general principles of the present invention may be more fully appreciated by reference to the following non-limiting examples.

EXAMPLE 1

Detection of HIV-1, Subtype B (HIV-1, IIIb) Pol Target Sequences Using SEQ ID NO:10 or SEQ ID NO:42 in Amplification Oligomer Mixture A sample of human plasma containing a known amount of HIV-1 subtype B (100 copies of HIV-1 IIIb per reaction tube) was mixed with an equal volume of a lysis buffer (790 mM HEPES, 230 mM succinic acid, 10% (w/v) lithium lauryl sulfate, 680 mM lithium hydroxide monohydrate). To capture the HIV-1 pol target RNA, the mixture also contained about 1.75 pmols each of oligomers of SEQ ID NO:4 and SEQ ID NO:6, and about 100 µg of immobilized poly-$dT_{14}$ probe attached to paramagnetic particles (0.7-1.05µ particles, Seradyn, Indianapolis, Ind.). Probes were attached to the particles using carbodiimide chemistry as previously described (Lund, et al., 1988, *Nuc. Acids Res.* 16:10861-10880). The mixture was heated at 55° C. to 60° C. for about 15 to 30 min and then cooled to room temperature to allow hybridization. Then a magnetic field was applied to attract the magnetic particles with the complex containing immobilized probe HIV-1, capture oligomer and HIV-1 RNA to a location on the reaction container (substantially as described in Wang, U.S. Pat. No. 4,895,650). The particles were then washed twice with 1 ml of a washing buffer (10 mM HEPES, 6.5 mM NaOH, 1 mM EDTA, 0.3% (v/v) ethanol, 0.02% (w/v) methyl-paraben, 0.01% (w/v) propyl-paraben, 150 mM NaCl, 0.1% (w/v) sodium lauryl sulfate) by resuspending the particles in the buffer and then repeating the magnetic separation step. Washed particles were then suspended in 75 µl of a nucleic acid amplification reagent solution for transcription-associated amplification using methods substantially as described previously (Kacian et al., U.S. Pat. Nos. 5,399,491 and 5,554,516).

Briefly, the washed particles with the attached complexes were mixed with 7.5 pmol each of amplification oligonucleotides that were either (1) SEQ ID NO:10, SEQ ID NO:11, SEQ ID NO:13 and SEQ ID NO:15, or (2) SEQ ID NO:42, SEQ ID NO:11, SEQ ID NO:13 and SEQ ID NO:15, in a reaction mixture (40 mM Trizma base, pH 7.5, 17.5 mM KCl, 20 mM $MgCl_2$, 5% polyvinylpyrrolidone (PVP), 1 mM each dNTP, 4 mM each rNTP), covered with a layer (200 µl) of inert oil to prevent evaporation, and incubated at 60° C. for 10-15 min, and then at 41.5-42° C. for 5 min. Enzymes (about 750 Units of reverse transcriptase and about 2,000 of Units T7 RNA polymerase per reaction) were added, mixed, and the target HIV-1 nucleic acid was amplified at 41.542° C. for 2 hr.

Amplified HIV-1 target sequences were detected using an AE-labeled probe (SEQ ID NO:17) which was detected by chemiluminescence and expressed in relative light units (RLU) substantially as described previously (U.S. Pat. No. 5,658,737 at column 25, lines 27-46; Nelson et al., 1996, *Biochem.* 35:8429-8438 at 8432). For each assay condition, negative controls consisted of all of the same reagents but substituting an equal volume of plasma that contained no HIV-1. The detected RLU of these assays for eleven HIV-1 positive ("HIV-1+") samples and eight HIV-1 negative samples for each set of amplification oligonucleotides are shown in Table 1.

TABLE 1

RLU Detected for Combinations of Amplification Oligonucleotides

| Sample | SEQ ID NO: 10, SEQ ID NO: 11, SEQ ID NO: 13 and SEQ ID NO: 15 | SEQ ID NO: 42, SEQ ID NO: 11, SEQ ID NO: 13 and SEQ ID NO: 15 |
|---|---|---|
| HIV-1+ | $2.11 \times 10^6$ | $1.90 \times 10^6$ |
| HIV-1+ | $1.69 \times 10^6$ | $1.88 \times 10^6$ |
| HIV-1+ | $1.67 \times 10^6$ | $1.86 \times 10^6$ |
| HIV-1+ | $1.63 \times 10^6$ | $1.78 \times 10^6$ |
| HIV-1+ | $1.47 \times 10^6$ | $1.74 \times 10^6$ |
| HIV-1+ | $1.47 \times 10^6$ | $1.73 \times 10^6$ |
| HIV-1+ | $1.42 \times 10^6$ | $1.71 \times 10^6$ |
| HIV-1+ | $1.24 \times 10^6$ | $1.64 \times 10^6$ |
| HIV-1+ | $1.18 \times 10^6$ | $1.54 \times 10^6$ |
| HIV-1+ | $1.17 \times 10^6$ | $1.44 \times 10^6$ |
| HIV-1+ | $1.13 \times 10^6$ | $1.22 \times 10^6$ |
| Average HIV-1+ | $1.47 \times 10^6$ | $1.68 \times 10^6$ |
| HIV-1 negative | $3.79 \times 10^3$ | $5.02 \times 10^3$ |
| HIV-1 negative | $3.57 \times 10^3$ | $4.95 \times 10^3$ |
| HIV-1 negative | $3.71 \times 10^3$ | $3.39 \times 10^3$ |
| HIV-1 negative | $2.73 \times 10^3$ | $3.00 \times 10^3$ |
| HIV-1 negative | $3.82 \times 10^3$ | $4.27 \times 10^3$ |
| HIV-1 negative | $4.67 \times 10^3$ | $4.49 \times 10^3$ |
| HIV-1 negative | $9.31 \times 10^3$ | $4.66 \times 10^3$ |
| HIV-1 negative | $3.81 \times 10^3$ | $3.91 \times 10^3$ |
| Average HIV-1 negative | $1.49 \times 10^3$ | $4.21 \times 10^3$ |

These results show that HIV-1 can be readily detected in a biological sample using the compositions and methods of the present invention. Moreover, the two different combinations of amplification oligomers were able to similarly amplify the captured pol target sequence to produce detectable amplified products. The next example shows that a different subtype, HIV-1 subtype C, can also be detected using the same combinations of capture oligomers, amplification oligomers and labeled probe.

EXAMPLE 2

Detection of HIV-1, Subtype C, Pol Target Sequences in Biological Samples

Samples of normal uninfected blood plasma were mixed with known amounts of HIV-1 subtype C RNA to produce samples containing about 100 copies of target nucleic acid per reaction. Negative controls were plasma samples without HIV-1 RNA that were treated identically in the assay. The samples were subjected to target capture, transcription-mediated amplification and labeled probe detection substantially as described in Example 1, and the results of these assays are shown in Table 2.

TABLE 2

RLU Detected for Amplification Oligonucleotides:

| Sample | SEQ ID NO: 10, SEQ ID NO: 11, SEQ ID NO: 13 and SEQ ID NO: 15 | SEQ ID NO: 42, SEQ ID NO: 11, SEQ ID NO: 13 and SEQ ID NO: 15 |
|---|---|---|
| HIV-1 subtype C+ | $4.49 \times 10^5$ | $6.63 \times 10^5$ |
| HIV-1 subtype C+ | $4.12 \times 10^5$ | $5.79 \times 10^5$ |
| HIV-1 subtype C+ | $4.07 \times 10^5$ | $4.61 \times 10^5$ |
| HIV-1 subtype C+ | $3.42 \times 10^5$ | $2.94 \times 10^5$ |
| HIV-1 subtype C+ | $3.42 \times 10^5$ | $2.72 \times 10^5$ |
| Average subtype C+ | $3.90 \times 10^5$ | $4.54 \times 10^5$ |
| HIV-1 neg. | $3.58 \times 10^4$ | $3.07 \times 10^3$ |
| HIV-1 neg. | $3.06 \times 10^3$ | $2.85 \times 10^3$ |
| HIV-1 neg. | $2.60 \times 10^3$ | $1.97 \times 10^3$ |
| HIV-1 neg. | $1.56 \times 10^4$ | $7.26 \times 10^3$ |
| Average of HIV-1 neg. | $1.42 \times 10^4$ | $3.79 \times 10^3$ |

Although the detected signals in these assays were somewhat lower than those of Example 1, these results show that the assay conditions also allow detection of HIV-1 subtype C nucleic acid in a biological sample.

The next example shows detection of HIV-1 target which is present in a biological sample at between 600 and 60 copies per ml.

EXAMPLE 3

Detection of Varying Copy Numbers of HIV-1 Subtype B (HIV-1 IIIb) Pol Target Sequences In this example, plasma samples containing a known number of copies of HIV-1 IIIb (600, 200 or 60 copies/ml) were assayed using the procedures substantially as described in Example 1, but using different combinations of amplification oligomers. In these assays, the transcription-mediated amplification was performed using either (1) SEQ ID NO:10, SEQ ID NO:11, SEQ ID NO:13 and SEQ ID NO:15, or (2) SEQ ID NO:10, SEQ ID NO:11, SEQ ID NO:43 and SEQ ID NO:15. Following the capture and amplification steps, the RLU signals shown in Table 3 were detected. Table 3 presents the average (mean) RLU and the standard deviation obtained from ten reactions for each of the different copy number samples (copy number=600, 200 or 60 per ml) tested, or from five reactions for the negative controls (copy number=0 per ml).

TABLE 3

Average RLU Detected for Amplification Oligonucleotides:

| HIV-1 Copies/ml of Sample | SEQ ID NO: 10, SEQ ID NO: 11, SEQ ID NO: 13 and SEQ ID NO: 15 | SEQ ID NO: 10, SEQ ID NO: 11, SEQ ID NO: 43 and SEQ ID NO: 15 |
|---|---|---|
| 600 | 373,464 ± 164,269 | 93,207 ± 70,948 |
| 200 | 74,695 ± 113,555 | 49,448 ± 49,938 |
| 60 | 22,838 ± 17,487 | 7,249 ± 8,876 |
| 0 | 1,861 ± 174 | 1,996 ± 180 |

In these assays, the combination of capture oligomer, amplification oligomers and detection labeled probe that included the amplification promoter-primer having the sequence of SEQ ID NO:13 provided higher detectable signals than the combination that included SEQ ID NO:43, but both combinations were able to detect the presence of at least 200 or more copies of HIV-1 per ml of sample. Moreover, the combination that included the primer of SEQ ID NO:13 was generally able to detect as low as 60 copies of HIV-1 per ml.

These assays were also performed in separate tests on samples containing 500 copies of HIV-1 IIIb per reaction. In these assays, the combination of capture oligomers, amplification oligomers and detection labeled probe that included the amplification promoter-primer having the sequence of SEQ ID NO:13 provided an average RLU signal for ten samples of $2.03 \times 10^6 \pm 7.03 \times 10^4$ compared to an average RLU signal of 1,624±174 for five negative controls. The combination of capture oligomers, amplification oligomers and detection labeled probe that included the amplification promoter-primer having the sequence of SEQ ID NO:43 provided an average RLU signal for ten samples of $1.30 \times 10^6 \pm 4.52 \times 10^5$ compared to an average RLU signal of 1,693±196 for four negative controls.

Other combinations of primers can also be used in a similar assay to detect HIV-1 in a biological sample as shown in the next example.

EXAMPLE 4

Detection of Varying Copy Numbers of HIV-1 Pol Target Sequences Using an Alternative Promoter-Primer Oligonucleotide In additional sets of experiments, plasma samples containing 200, 100 or 20 copies of HIV-1 IIIb per reaction were tested using a similar combination of capture oligomers, amplification oligomers and detection labeled probe as one embodiment described in Example 3, but using a promoter-primer having the sequence of SEQ ID NO:44 in place of the primer having the sequence of SEQ ID NO:15 in the amplification reaction mixture. That is, target capture, amplification and detection steps were performed substantially as described in Example 1, but the amplification oligonucleotides used in the amplification reactions included those having the sequences of SEQ ID NO:10, SEQ ID NO:11, SEQ ID NO:13 and SEQ ID NO:44.

The results of these assays are shown in Table 4, in which the average (mean) detected RLU are shown for each of the sets of assays.

TABLE 4

Detection of Different Numbers of HIV-1 Target in a Sample

| Experiment No. | HIV-1 Copies Per Reaction | Mean RLU | Samples tested |
|---|---|---|---|
| 1 | 200 | $1.59 \times 10^6$ | 5 |
| 1 | 20 | $1.25 \times 10^5$ | 5 |
| 1 | 0 (background) | $1.46 \times 10^3$ | 3 |
| 2 | 200 | $1.10 \times 10^6$ | 5 |
| 2 | 20 | $1.79 \times 10^5$ | 5 |
| 2 | 0 (background) | $1.47 \times 10^3$ | 2 |
| 3 | 100 | $2.54 \times 10^6$ | 5 |
| 3 | 20 | $2.49 \times 10^6$ | 5 |
| 3 | 0 (background) | $2.94 \times 10^3$ | 2 |

These results show that the assay can detect as few as 20 copies of HIV-1 target nucleic acid in a biological sample.

The following examples show that a similar assay using capture oligomers, amplification oligonucleotides and labeled probes specific for the LTR target region of HIV-1 can also be used to detect HIV-1 target nucleic acid in a biological sample.

EXAMPLE 5

Detection of HIV-1 LTR Sequences

This assay used different capture oligomers to capture the target HIV-1 RNA, which was present in the sample at known numbers of copies, and then amplify the HIV-1 sequences using amplification oligomers (SEQ ID NO: 8 and SEQ ID NO:9) specific for the LTR region, as diagramed in FIG. 1. The amplified sequences were then detected using a labeled probe that specifically bound to LTR sequences (SEQ ID NO:41). The HIV-1 target RNA was present in tested samples made of 500 µl human plasma containing 1,000, 200 or 50 copies of HIV-1, and compared to negative samples of plasma containing no HIV-1 RNA which were tested under the same conditions. For each set of conditions, six samples were tested.

The protocol used was substantially as described in Example 1 with the following changes. Target capture was performed using capture oligomers having SEQ ID NO: 2 (LTR specific, 2 pmol/reaction), SEQ ID NO: 20 (LTR specific, 2 pmol/reaction) or a mixture of SEQ IN NO:4 and SEQ ID NO:6 (both pol specific, 1.75 pmol each/reaction) and using oligo-dT$_{14}$ oligonucleotides attached to magnetic particles substantially as described in Example 1. The mixture of sample, capture oligomers and immobilized probes on magnetic particles was heated to 60° C. for 20 min, cooled to room temperature for 20 min and then the magnetic particles and their attached complexes were separated and washed twice. Following target capture and washing, amplification was carried out substantially as described in Example 1, using 75 µl of amplification reagents without enzymes and containing amplification oligonucleotides having SEQ ID NO: 8 and SEQ ID NO:9, which was overlaid with 100 µl of oil, heated at 65° C. for 10 min and then incubated at 41.5-42° C. for 5 min. The enzymes were added (25 µl) and the amplification reaction was incubated 1 hr at 42° C. Then 100 µl of probe reagent containing 0.1 pmol/reaction of oligomer having SEQ ID NO:41 was added and the mixture was heated at 60° C. for 15 min, followed by addition of 300 µl of selection reagent, incubation at 60° C. for 10 min, cooling to room temperature and detection of relative light units ("RLU" for 2 sec) in a luminometer (e.g., LEADER®, Gen-Probe, Inc., San Diego, Calif.) (substantially as described in U.S. Pat. No. 5,658,737 at column 25, lines 27-46; and Nelson et al., *Biochem.* 35:8429-8438(1996) at page 8432).

The results of these assays are shown in Table 5, reporting the average RLU (mean±standard deviation) for each of the test conditions of six samples each. The detected RLU are reported for each group containing different numbers of HIV-1 target (1,000, 200 or 50 copies) compared to 0 copies in the negative ("Neg.") controls.

different capture oligomers for the LTR region (SEQ ID NO:2 and SEQ ID NO:20) were both effective in generating positive signals from HIV-1-containing biological samples compared to HIV-1-negative samples.

The next example shows different variations of capture oligomers used to detect HIV-1 subtype B and Group O sequences.

EXAMPLE 6

Detection of LTR Regions of HIV-1 Subtype B and Group O

The assays in this example were performed substantially as described in Example 5, except that another capture oligomer was used that is specific for the HIV-1 LTR region, having a sequence (SEQ ID NO:45) that varies from that of SEQ ID NO:2 by one base (A instead of T at position 9). The HIV-1 target nucleic acid in different plasma samples was either Subtype B (1,000 or 100 copies per assay) or Group O (MVP5180 virion at 1,000 or 100 copies per assay).

The samples (six per assay condition) were treated, substantially as described in Example 5, with capture oligomers having sequences of SEQ ID NO:2, SEQ ID NO:45 or the mixture of SEQ ID NO:4 and SEQ ID NO:6. Amplification was done substantially as described in Example 6, and the signals resulting from binding of an acridinium-labeled probe

TABLE 5

LTR Amplification and Detection

| Capture Oligomers | 1,000 Copies HIV-1 | 200 Copies HIV-1 | 50 Copies HIV-1 | 0 Copies (Negative) |
|---|---|---|---|---|
| SEQ ID NO: 2 | $1.61 \times 10^6 \pm 4.07 \times 10^5$ | $2.47 \times 10^5 \pm 2.38 \times 10^5$ | $7.27 \times 10^4 \pm 5.93 \times 10^4$ | $3.38 \times 10^3 \pm 4.02 \times 10^2$ |
| SEQ ID NO: 20 | $2.15 \times 10^5 \pm 2.24 \times 10^5$ | $4.18 \times 10^4 \pm 4.30 \times 10^4$ | $1.04 \times 10^4 \pm 1.00 \times 10^4$ | $5.02 \times 10^4 \pm 1.25 \times 10^3$ |
| SEQ ID NO: 4 + SEQ ID NO: 6 | $1.40 \times 10^6 \pm 3.52 \times 10^5$ | $4.75 \times 10^5 \pm 2.49 \times 10^5$ | $5.15 \times 10^4 \pm 4.51 \times 10^4$ | $2.92 \times 10^3 \pm 5.34 \times 10^2$ |

The results in Table 5 show that the target nucleic acid can be captured by oligomers specific for the region to be amplified (e.g., LTR, rows 2 and 3) or by capture oligomers specific for another region (e.g., Pol, row 4). The results also show that having the sequence of SEQ ID NO:16 to the amplified sequences were detected as described in Example 5. The average RLU (mean±standard deviation) for the six samples for each of the assay conditions are shown in Table 6.

TABLE 6

LTR HIV-1 Detection of Subtype B and Group O Viral RNA

| Target & Amount in Sample | Capture Oligomer SEQ ID NO: 2 (T at residue 9) | Capture Oligomer SEQ ID NO: 45 (A at residue 9) | Capture Oligomers SEQ ID NO: 4 + SEQ ID NO: 6 |
|---|---|---|---|
| Subtype B 1000 copies | $5.49 \times 10^6 \pm 2.21 \times 10^6$ | $6.24 \times 10^6 \pm 1.44 \times 10^5$ | $5.41 \times 10^6 \pm 2.65 \times 10^6$ |
| Subtype B 100 copies | $1.87 \times 10^6 \pm 2.42 \times 10^6$ | $2.54 \times 10^6 \pm 1.90 \times 10^6$ | $3.40 \times 10^6 \pm 2.09 \times 10^6$ |
| Subtype B 0 copies | $3.31 \times 10^3 \pm 6.72 \times 10^2$ | $3.14 \times 10^3 \pm 5.14 \times 10^2$ | $3.23 \times 10^3 \pm 1.10 \times 10^2$ |
| Group O 1000 copies | $4.13 \times 10^6 \pm 1.12 \times 10^6$ | $4.13 \times 10^6 \pm 1.13 \times 10^6$ | $3.65 \times 10^6 \pm 1.33 \times 10^6$ |
| Group O 100 copies | $3.29 \times 10^5 \pm 3.69 \times 10^5$ | $6.78 \times 10^5 \pm 7.19 \times 10^5$ | $8.65 \times 10^5 \pm 1.38 \times 10^6$ |
| Group O 0 copies | $3.24 \times 10^3 \pm 4.99 \times 10^2$ | $2.98 \times 10^3 \pm 7.53 \times 10^2$ | $3.14 \times 10^3 \pm 2.13 \times 10^2$ |

These results show that modified capture oligomers such as that of SEQ ID NO:45 are effective in an assay that amplifies and detects the captured HIV-1 target, including Group O HIV-1 target sequences. In additional assays, capture oligomers that were a mixture of oligomers having sequences of SEQ ID NO:2 and SEQ ID NO:45 (i.e., synthetic oligomers in which position 9 was either A or T) were also effective in assays to detect HIV-1, including Group O. This example also shows that capture of the target HIV-1 nucleic acid may be performed using capture oligomers specific for one region (e.g., pol) and then amplified and detected with oligonucleotide primers and probe that are specific for another region (e.g., LTR).

The next example shows that different combinations of promoter-primers and non-T7 primers can be used to amplify HIV-1 LTR target sequences to produce detectable amplification products from a biological sample containing HIV-1.

EXAMPLE 7

Comparison of HIV-1 LTR Amplification Using Different Combinations of Primers

HIV-1 RNA purified from high titer tissue culture specimens was mixed with amplification reagents at known numbers of copies of HIV-1 for testing different combinations of amplification oligonucleotides in assays that used the amplification and detection steps substantially as described in Example 5. The biological samples contained 10,000, 1,000, 250 or 100 copies of HIV-1 per reaction, and were compared to negative controls (human plasma containing no HIV-1 RNA). These samples were amplified in seven replicate tests for each pair of amplification oligomers tested (about 1.5 to 2.0 pmol of each primer per assay). The combinations of primers used were: a T7 promoter-primer having the sequence of SEQ ID NO:8 combined with a non-T7 primer having the sequence of SEQ ID NO:9, SEQ ID NO:35, SEQ ID NO:36, SEQ ID NO:37 or SEQ ID NO:38; and a T7 promoter-primer having the sequence of SEQ ID NO:30 combined with a non-T7 primer having the sequence of SEQ ID NO:9, SEQ ID NO:35, SEQ ID NO:36, SEQ ID NO:37 or SEQ ID NO:38. For each of these ten combinations, the biological samples that contained 100 or more copies of target HIV-1 produced a positive detectable signal in the assay. That is, amplified sequences were produced and then detected using a labeled LTR-specific probe (SEQ ID NO:16 or SEQ ID NO:41), producing a signal of $10^5$ to $10^6$ RLU (mean of seven samples per assay condition), compared to the negative controls that produced less than $10^3$ RLU (mean) under the same conditions. For comparison, the HIV-1-positive samples were also amplified using a combination of pol-specific amplification oligomers (SEQ ID NO:10 and SEQ ID NO:13), which also produced a detectable average RLU signal of $10^5$ to $10^6$ for all of the HIV-1-positive samples.

In additional assays, greater dilutions of the HIV-1 target nucleic acid were amplified using the SEQ ID NO:8 promoter-primer combined with a primer having the sequence of SEQ ID NO:9, SEQ ID NO:35, SEQ ID NO:36, SEQ ID NO:37 or SEQ ID NO:38. In these tests, the HIV-1 virion RNA was present at 100, 50, 30 or 10 copies per assay. Amplified sequences were detected at an average of $10^5$ to $10^6$ RLU when at least 30 copies of HIV-1 virion RNA were present in the sample. At 10 copies of HIV-1 per sample, the detected RLU indicating amplified LTR sequences ($10^4$ to $10^5$ average) were at least 10-fold higher than those of the negative controls (averaging less than $10^3$ RLU).

In separate assays, using HIV-1 target nucleic acid present at 100, 50, 30 or 10 copies per sample, the LTR target sequences were amplified using a promoter primer having SEQ ID NO:32 and a non-T7 primer having the sequence of SEQ ID NO:9, SEQ ID NO:35, SEQ ID NO:36, SEQ ID NO:37 or SEQ ID NO:38. In these assays, the combinations of a primer having SEQ ID NO:32 and a primer having SEQ ID NO:9, SEQ ID NO:35 or SEQ ID NO:36 produced about $10^4$ to $10^5$ RLU (average) when 50 to 100 copies of target were present, whereas the combinations of a primer having SEQ ID NO:32 and a primer having SEQ ID NO:37 or SEQ ID NO:38 produced about $10^3$ to $10^4$ RLU (average) when 50 to 100 copies of target were present, all compared to negative controls of less than 400 RLU.

HIV-1 target nucleic acid present at 100, 50, 30 or 10 copies per sample were also amplified using combinations of a promoter-primer having the sequence of SEQ ID NO:34 and the non-T7 primers tested above (SEQ ID NO:9, SEQ ID NO:35, SEQ ID NO:36, SEQ ID NO:37 or SEQ ID NO:38). In these assays, the combinations of a primer having SEQ ID NO:34 and a primer having SEQ ID NO:9 or SEQ ID NO:36 produced about $10^5$ RLU (average) when 50 to 100 copies of target were present, whereas the combinations of a primer having SEQ ID NO:34 and a primer having SEQ ID NO:35, SEQ ID NO:37 or SEQ ID NO:38 produced about $10^3$ to $10^4$ RLU (average) when 50 to 100 copies of target were present, all compared to negative controls of less than $10^3$ RLU.

Based on these results and additional tests, preferred combinations of amplification oligonucleotides for amplifying HIV-1 LTR sequences include: SEQ ID NO:8 and SEQ ID NO:35; SEQ ID NO:8 and SEQ ID NO:9; SEQ ID NO:8 and SEQ ID NO:36; SEQ ID NO:30 and SEQ ID NO:9; SEQ ID NO:30 and SEQ ID NO:36; SEQ ID NO:32 and SEQ ID NO:9; and SEQ ID NO:34 and SEQ ID NO:36.

The next example shows that both pol-specific and LTR-specific assays can detect HIV-1 subtype B and Group O nucleic acids in biological samples.

EXAMPLE 8

Assay for HIV-1 Subtype B and Group O Nucleic Acids

In these tests, LTR target sequences were amplified and detected for different HIV-1 isolates. Plasma samples containing known numbers of copies of HIV-1 were prepared using subtype B (1,000, 100 or 30 copies of virion RNA per assay) or two Group O isolates (CA9 and MVP5180, purified individually from high titer tissue culture and used at dilutions equivalent to about 1,000, 100 or 30 copies per assay). The samples were subjected to target capture using the methods substantially as described in Example 5, using capture oligomers having sequences of SEQ ID NO:2 (LTR-specific), and SEQ ID NO:4 and SEQ ID NO:6 (both pol-specific). Then the captured target was amplified using substantially the procedures described in Example 5, using a LTR-specific promoter-primer having the sequence of SEQ ID NO:8 and a LTR-specific primer having the sequence of SEQ ID NO:9. The amplified sequences were detected using an AE-labeled probe (0.1 pmol/reaction) having the sequence of SEQ ID NO:16 as described above. The average RLU detected (mean±standard deviation) for five samples for each set of conditions are presented in Table 7.

TABLE 7

Amplified and Detected (RLU) HIV-1 LTR Sequences of Subtype B and Group O

| Target Amount | Subtype B | Group O Strain MVP5180 | Group O Strain CA9 |
|---|---|---|---|
| 1,000 copies | $7.72 \times 10^6 \pm 7.10 \times 10^5$ | $8.00 \times 10^6 \pm 4.56 \times 10^5$ | $7.04 \times 10^6 \pm 1.76 \times 10^6$ |
| 100 copies | $4.84 \times 10^6 \pm 2.14 \times 10^6$ | $7.45 \times 10^6 \pm 5.21 \times 10^5$ | $5.91 \times 10^5 \pm 1.23 \times 10^6$ |
| 30 copies | $3.81 \times 10^5 \pm 3.56 \times 10^5$ | $1.13 \times 10^6 \pm 1.56 \times 10^6$ | $5.52 \times 10^4 \pm 6.96 \times 10^4$ |
| 0 copies | $7.15 \times 10^3 \pm 7.38 \times 10^2$ | $6.98 \times 10^3 \pm 3.71 \times 10^3$ | $5.80 \times 10^3 \pm 1.12 \times 10^3$ |

These results show that the assay can detect both subtype B and Group O HIV-1 and can detect different Group O strains using HIV-1 LTR-specific primers and probe.

A similar assay was used to detect both LTR and pol sequences in the same amplification mixture. In this assay, the same target HIV-1 nucleic acids were used at the same concentrations and target capture was performed using a mixture of capture oligomers that included the LTR-specific oligomer having SEQ ID NO:2 and two pol-specific oligomers having SEQ ID NO:4 and SEQ ID NO:6. During amplification as described above, a combination of primers was used that included LTR-specific primers having the sequences of SEQ ID NO:8 and SEQ ID NO:9, and pol-specific primers having the sequences of SEQ ID NO:10, SEQ ID NO:11, SEQ ID NO:13 and SEQ ID NO:15. This multiplex amplification reaction includes multiple primers for different targets in the same amplification reagent to simultaneously amplify the target nucleic acids. Following amplification, the amplified sequences were detected independently using LTR-specific AE-labeled probe having SEQ ID NO:16, or pol-specific AE-labeled probe having SEQ ID NO:17, using 0.1 pmol/µl of each in the standard protocol as described in Example 1. The results of these tests are shown in Table 8, showing the average RLU (mean±standard deviation) for five samples for each set of assay conditions.

TABLE 8

Detection of HIV-1 LTR and Pol Sequences Following Multiplex Amplification

| Subtype/Group (Strain), Target Amount or Dilution Factor | LTR Detection | Pol Detection |
|---|---|---|
| Subtype B 1,000 copies | $7.78 \times 10^6 \pm 4.75 \times 10^5$ | $4.10 \times 10^6 \pm 9.81 \times 10^4$ |
| Subtype B 100 copies | $1.57 \times 10^6 \pm 1.36 \times 10^6$ | $2.99 \times 10^6 \pm 1.65 \times 10^6$ |
| Subtype B 30 copies | $3.20 \times 10^5 \pm 2.70 \times 10^5$ | $3.09 \times 10^6 \pm 1.07 \times 10^6$ |
| Subtype B 0 copies (negative control) | $3.71 \times 10^3 \pm 4.01 \times 10^2$ | $1.19 \times 10^3 \pm 2.81 \times 10^2$ |
| Group O (Strain MVP5180) 1,000 copies | $7.92 \times 10^6 \pm 3.07 \times 10^5$ | $1.79 \times 10^6 \pm 3.34 \times 10^5$ |
| Group O (Strain MVP5180) 100 copies | $3.64 \times 10^6 \pm 1.79 \times 10^6$ | $2.16 \times 10^5 \pm 2.49 \times 10^5$ |
| Group O (Strain MVP5180) 30 copies | $2.28 \times 10^5 \pm 2.16 \times 10^5$ | $3.22 \times 10^4 \pm 4.90 \times 10^4$ |
| Group O (Strain MVP5180) 0 copies (negative control) | $5.06 \times 10^3 \pm 3.13 \times 10^2$ | $1.64 \times 10^3 \pm 9.52 \times 10^2$ |
| Group O (Strain CA9) 1,000 copies | $1.94 \times 10^6 \pm 4.12 \times 10^5$ | $1.38 \times 10^6 \pm 1.21 \times 10^6$ |
| Group O (Strain CA9) 100 copies | $3.67 \times 10^5 \pm 6.25 \times 10^5$ | $3.10 \times 10^5 \pm 6.16 \times 10^5$ |
| Group O (Strain CA9) 30 copies | $2.20 \times 10^5 \pm 4.58 \times 10^5$ | $1.27 \times 10^3 \pm 39$ |
| Group O 0 copies (negative control) | $3.64 \times 10^3 \pm 3.20 \times 10^2$ | $1.24 \times 10^3 \pm 75$ |

These results show that amplified sequences specific for both the HIV-1 LTR and pol regions were produced during the multiplex amplification and the amplified sequences were detected using LTR-specific or pol-specific probes, respectively. In similar experiments, a combination of labeled probes having sequences of SEQ ID NO:16, SEQ ID NO:17 and SEQ ID NO:18 were used to successfully detect the amplified HIV-1 sequences of both subtype B and Group O isolates. In separate experiments, similar effective detection was accomplished using a labeled probe having SEQ ID NO:16 with an inosine at position 7.

Similar results were obtained in separate experiments in which the amplified target region was HIV-1 pol sequences from subtype B and Group O, probed with a 2-methyl-AE labeled probe having SEQ ID NO:17. In these experiments, the target was initially present at 1,000, 100, 50, 20 or 10 copies per reaction, compared to a negative control containing no target. Five replicate assays were performed for each reaction condition. For HIV-1 subtype B, the mean RLU detected was in a range of $9.20 \times 10^5$ to $4.44 \times 10^5$ for reactions containing target, compared to a mean RLU of $1.97 \times 10^3$ for the negative controls. For HIV-1 Group O, the mean RLU detected was in a range of $3.53 \times 10^5$ to $1.69 \times 10^4$ for reactions containing 1,000 to 50 copies of target, with variable results obtained for tubes containing 20 or 10 copies of target, compared to a mean RLU of $2.60 \times 10^3$ for the negative controls.

These results all show that different groups of HIV-1 can be detected using target capture and amplification of sequences using the combinations of capture probes, primers and detection probes described herein. Use of additional combinations are described in Examples 9 and 10.

EXAMPLE 9

Assay for HIV-1 Pol Target Nucleic Acids in HIV-1 Subtype B and Group O

In a series of tests, HIV-1 of subtype B and Group O were assayed substantially as described in the previous examples, using different probes. The samples were subjected to target capture using the methods substantially as described in Example 1, using pol-specific capture oligomers having sequences of SEQ ID NO:4 and SEQ ID NO:6. Then the captured HIV-1 target was amplified using substantially the procedures described in Example 1, using a combination of promoter-primers having the sequences of SEQ ID NO:13 and SEQ ID NO:15 and a combination of primers having the sequences of SEQ ID NO:10 and SEQ ID NO:11. These experiments compared detection with different HIV-1-specific probes. The reactions were performed using HIV-1 subtype B at $10^4$ copies/ml and Group O at $10^6$ copies/ml. Following amplification and before detection, the amplification reactions for each set of assays were pooled and then diluted as indicated in Table 9. At limiting dilutions, the RLU detected was equivalent to background (data not shown). For each assay reported in Table 9, ten individual detection assays were performed and the mean number of RLU detected±standard deviation are presented.

The amplified pol sequences were detected as described earlier using 2-methyl-AE labeled probes (0.1 pmol/reaction) having the sequence of SEQ ID NO:18 or SEQ ID NO:46, using different lots of the probe having SEQ ID NO:46, labeled between residues 10 and 11 (Lot 1) or residues 7 and 8 (Lot 2).

amplified and detected using probes having sequences of SEQ ID NO:50 or SEQ ID NO:53 and compared to results with the previously tested SEQ ID NO:17 probe. In these experiments, capture of the target RNA was not included and the sample tubes were prepared containing $10^4$ copies of either HIV-1 subtype B or HIV-1 Group O (five tubes for each type, with a negative control containing no HIV-1 RNA) in an amplification reaction mixture containing 40 mM Trizma base (pH 7.5), 17.5 mM KCl, 20 mM $MgCl_2$, 5% PVP, 1 mM each dNTP and 4 mM each rNTP. Transcription-mediated amplification was performed substantially as described in Example 1, except that incubation temperatures were 65° C. for 10 min, and then 42° C. for 10 min before addition of enzymes, followed by amplification for 1 hr using primers having the sequences of SEQ ID NO:10, SEQ ID NO:11, SEQ ID NO:13 and SEQ ID NO:15. Following amplification, the products were pooled to minimize variation between different amplification tubes, making separate pools for the different HIV-1 strains. The pooled amplification products were used without dilution (i.e., about $10^4$ copies of target in the sample) or serially diluted into 2× Hybridization Buffer (see Example 1) as shown in Table 10, to provide the equivalent of $10^3$, $10^2$, 10 or 1 copies of target in the sample. The tubes were then used for hybridization at 60° C. for 15 min with AE-labeled probes having SEQ ID NO: 50, SEQ ID NO:53 or SEQ ID NO:17. Following treatment of the hybridization tubes at 60° C. for 10 min with the selection reagent to selectively inactivate unbound probe, chemiluminescence was detected as described above. Mean RLU for each of the hybridization reactions are shown in Table 10.

TABLE 9

Comparison of Pol-specific Probes for Detecting HIV-1 Subtype B and Group O

| Target, Dilution Factor Assay Number | SEQ ID NO: 46 Probe (Lot 1) | SEQ ID NO: 46 Probe (Lot 2) | SEQ ID NO: 18 Probe |
|---|---|---|---|
| Subtype B, $10^{-1}$ Dilution Assay 1 | $1.05 \times 10^5 \pm 2.66 \times 10^3$ | $9.83 \times 10^4 \pm 2.90 \times 10^3$ | $1.00 \times 10^5 \pm 2.20 \times 10^3$ |
| Subtype B, $10^{-1}$ Dilution Assay 2 | $9.62 \times 10^4 \pm 4.88 \times 10^3$ | $9.57 \times 10^4 \pm 4.40 \times 10^3$ | $9.91 \times 10^4 \pm 2.54 \times 10^3$ |
| Group O, $10^{-1}$ Dilution Assay 3 | $8.66 \times 10^5 \pm 1.69 \times 10^4$ | $7.11 \times 10^5 \pm 1.43 \times 10^4$ | $6.61 \times 10^5 \pm 1.51 \times 10^4$ |
| Group O, $10^{-2}$ Dilution Assay 4 | $3.41 \times 10^5 \pm 1.15 \times 10^4$ | $2.53 \times 10^5 \pm 1.08 \times 10^4$ | $4.77 \times 10^5 \pm 1.32 \times 10^4$ |

The results of these experiments show that different labeled probes can effectively detect both HIV-1 subtype B and Group O amplified target sequences. In separate experiments using similar experimental protocols, probes having SEQ ID NO:46 labeled with 2-methyl-AE between residues 6 and 7, 7 and 8, or 10 and 11 were all effective in detecting HIV-1 subtype B and Group O amplified target sequences. These experiments show that a variety of different labeled probes may be used in these detection assays for detecting different groups of HIV-1.

EXAMPLE 10

Assay for HIV-1 Pol Target Nucleic Acids in HIV-1 Subtype B and Group O

In experiments similar to those described in Example 9, HIV-1 target sequences from subtype B and Group O were

TABLE 10

Detected RLU for Amplified HIV-1 Pol Sequences with Different Probes

| Target, Copies per Sample | SEQ ID NO: 50 | SEQ ID NO: 53 | SEQ ID NO: 17 |
|---|---|---|---|
| Subtype B, $10^4$ | $2.14 \times 10^5$ | $4.39 \times 10^5$ | $3.71 \times 10^5$ |
| Subtype B, $10^3$ | $8.11 \times 10^4$ | $2.40 \times 10^5$ | $2.21 \times 10^5$ |
| Subtype B, $10^2$ | $6.84 \times 10^4$ | $2.15 \times 10^5$ | $2.01 \times 10^5$ |
| Subtype B, 10 | $6.45 \times 10^4$ | $2.24 \times 10^5$ | $1.40 \times 10^5$ |
| Subtype B, 1 | $2.37 \times 10^4$ | $8.51 \times 10^4$ | $2.31 \times 10^4$ |
| Group O, $10^4$ | $7.50 \times 10^4$ | $4.23 \times 10^5$ | $2.89 \times 10^5$ |
| Group O, $10^3$ | $2.74 \times 10^4$ | $2.16 \times 10^5$ | $1.71 \times 10^5$ |
| Group O, $10^2$ | $1.43 \times 10^4$ | $1.26 \times 10^5$ | $5.15 \times 10^4$ |
| Group O, 10 | $7.20 \times 10^3$ | $2.93 \times 10^4$ | $7.65 \times 10^3$ |
| Group O, 1 | $5.90 \times 10^3$ | $5.78 \times 10^3$ | not determined |

As in Example 9 and by comparison with those results, the results of Table 10 show that different groups of HIV-1 can be detected using different pol-specific probes. In these and additional experiments, probes having SEQ ID NO:53 were shown to be effective in detecting HIV-1 pol amplified sequences when labeled at a variety of positions in the probe (e.g., between residues 5 and 6, or residues 6 and 7, or residues 13 and 14). Similarly, probes having SEQ ID NO:17 were effective in detecting HIV-1 amplified sequences when labeled at a variety of positions (e.g., between residues 6 and 7, or residues 7 and 8, or residues 10 and 11). Thus, different probes exemplified by these experimental results are effective for detecting amplified HIV-1 sequences.

Although the present invention has been described in the context of particular examples and preferred embodiments, it will be understood that the invention is not limited to such embodiments. Instead, the scope of the present invention shall be measured by the claims that follow.

We claim:

1. A method of detecting HIV-1 nucleic acid in a biological sample, comprising the steps of:
    contacting a biological sample containing HIV-1 nucleic acid with at least one capture oligomer comprising a base sequence that hybridizes specifically to a target region in LTR or pol sequences of HIV-1 nucleic acid, thus forming a capture oligomer:HIV-1 nucleic acid complex;
    separating the capture oligomer:HIV-1 nucleic acid complex from the biological sample;
    amplifying LTR sequences, or a cDNA made therefrom, by using at least two amplification oligomers, wherein a first amplification oligomer is selected from the group consisting of SEQ ID NO:29, SEQ ID NO:30, SEQ ID NO:31, and SEQ ID NO:32, and wherein a second amplification oligomer is selected from the group consisting of SEQ ID NO:35, SEQ ID NO:36, SEQ ID NO:37 and SEQ ID NO:38, and a nucleic acid polymerase in vitro to produce an amplified product; and
    detecting the amplified product using a labeled detection probe that hybridizes specifically with the amplified product, thereby indicating presence of the HIV-1 nucleic acid in the biological sample.

2. The method of claim 1, wherein the contacting step uses a capture oligomer that hybridizes specifically to a target region in LTR sequences of HIV-1 nucleic acid complementary to SEQ ID NO:1 or SEQ ID NO:57, or complementary to LTR-specific contained in SEQ ID NO:2 or SEQ ID NO:45.

3. The method of claim 1, wherein the contacting step further comprises using a capture oligomer that hybridizes specifically to a target region in pol sequences of HIV-1 nucleic acid.

4. The method of claim 1, wherein the amplifying step uses at least two amplification oligomers, wherein the first amplification oligomer is a promoter primer having the sequence of SEQ ID NO:30 or SEQ ID NO:32, and the second amplification oligomer is a primer having the sequence of SEQ ID NO:35, SEQ ID NO:36, SEQ ID NO:37, or SEQ ID NO:38.

5. The method of claim 4, wherein the amplifying step uses any of the following combinations of promoter-primers and primers:
    the promoter-primer consisting essentially of SEQ ID NO:30 with the primer consisting essentially of SEQ ID NO:35;
    the promoter-primer consisting essentially of SEQ ID NO:30 with the primer consisting essentially of SEQ ID NO:36;
    the promoter-primer consisting essentially of SEQ ID NO:30 with the primer consisting essentially of SEQ ID NO:37;
    the promoter-primer consisting essentially of SEQ ID NO:30 with the primer consisting essentially of SEQ ID NO:38;
    the promoter-primer consisting essentially of SEQ ID NO:32 with the primer consisting essentially of SEQ ID NO:35;
    the promoter-primer consisting essentially of SEQ ID NO:32 with the primer consisting essentially of SEQ ID NO:36;
    the promoter-primer consisting essentially of SEQ ID NO:32 with the primer consisting essentially of SEQ ID NO:37; and
    the promoter-primer consisting essentially of SEQ ID NO:32 with the primer consisting essentially of SEQ ID NO:38.

6. The method of claim 1, wherein the amplifying step further uses at least two amplification oligomers that bind specifically to HIV-1 pol sequences or to sequences complementary to HIV-1 pol sequences.

7. The method of claim 6, wherein the amplifying step uses at least two amplification oligomers for amplifying pol sequences selected from the group consisting of: SEQ ID NO:10, SEQ ID NO:11, SEQ ID NO:13, SEQ ID NO:14, SEQ ID NO:15, SEQ ID NO:42, SEQ ID NO:43, and SEQ ID NO:44.

8. The method of claim 1, wherein the detecting step uses at least one labeled detection probe having an LTR-specific sequence consisting essentially of SEQ ID NO:16, SEQ ID NO:39, SEQ ID NO:40, or SEQ ID NO:41.

9. The method of claim 1, wherein the detecting step uses a combination of at least two labeled detection probes made up of a first probe having a sequence consisting essentially of SEQ ID NO:16 and a second probe having a sequence consisting essentially of SEQ ID NO:41.

10. The method of claim 1, wherein the detecting step uses a combination of at least two labeled detection probes made up of a first probe sequence that is about 20 bases containing a sequence of 18 bases contained in SEQ ID NO:39, and a second probe sequence that is about 20 bases containing a sequence of 14 bases contained in SEQ ID NO:40.

11. The method of claim 1, wherein the detecting step uses a combination of at least two labeled detection probes made up of at least one probe that has a sequence of about 20 bases consisting essentially of SEQ ID NO:16 and at least one probe that has a pol-specific sequence.

12. The method of claim 1, wherein the detecting step uses at least one labeled detection probe that includes at least one 2'-methoxy backbone linkage.

13. A kit comprising a combination of at least two oligomers, wherein LTR-specific oligomers contained in the kit are selected from the group consisting of SEQ ID NO:29, SEQ ID NO:30, SEQ ID NO:31, SEQ ID NO:32, SEQ ID NO:35, SEQ ID NO:36, SEQ ID NO:37 and SEQ ID NO:38.

14. The kit of claim 13, further comprising at least one oligomer having an LTR-specific sequence consisting essentially of SEQ ID NO:16, SEQ ID NO:39, SEQ ID NO:40, or SEQ ID NO:41.

15. A composition comprising a combination of at least two oligomers, wherein a first oligomer is selected from the group consisting of:
- SEQ ID NO:29, optionally with a promoter sequence covalently attached to the 5' end of SEQ ID NO:29;
- SEQ ID NO:31, optionally with a promoter sequence covalently attached to the 5' end of SEQ ID NO:31;
- SEQ ID NO:30; and
- SEQ ID NO:32, and wherein a second oligomer is selected from the group consisting of SEQ ID NO:35, SEQ ID NO:36, SEQ ID NO:37 and SEQ ID NO:38.

16. The composition of claim 15, wherein the promoter sequence is a T7 RNA polymerase promoter sequence.

17. The composition of claim 15, wherein the composition further comprises an oligomer of SEQ ID NO:16, SEQ ID NO:39, SEQ ID NO:40, SEQ ID NO:41, or a mixture of oligomers of SEQ ID NO:16 and SEQ ID NO:41.

18. The composition of claim 15, wherein an oligomer base sequence is linked by a backbone that includes at least one 2'-methoxy RNA group, at least one 2' fluoro-substituted RNA group, at least one peptide nucleic acid linkage, at least one phosphorothioate linkage, at least one methylphosphonate linkage or any combination thereof.

19. The composition of claim 17, wherein the oligomer or an oligomer in the mixture of oligomers comprises at least one 2'-methoxy RNA group in the backbone.

20. The composition of claim 17, wherein the oligomer or an oligomer in the mixture of oligomers is linked to a detectable label.

* * * * *

SEQUENCE LISTING

```
<160> NUMBER OF SEQ ID NOS: 57

<210> SEQ ID NO 1
<211> LENGTH: 22
<212> TYPE: DNA
<213> ORGANISM: Artificial Sequence
<220> FEATURE:
<223> OTHER INFORMATION: synthetic capture oligomer

<400> SEQUENCE: 1
actgacgctc tcgcacccat ct                                              22

<210> SEQ ID NO 2
<211> LENGTH: 54
<212> TYPE: DNA
<213> ORGANISM: Artificial Sequence
<220> FEATURE:
<223> OTHER INFORMATION: synthetic capture oligomer with 3' tail
      sequence
<220> FEATURE:
<221> NAME/KEY: misc_structure
<222> LOCATION: (23)..(54)
<223> OTHER INFORMATION: 3' tail sequence

<400> SEQUENCE: 2
actgacgctc tcgcacccat ctttaaaaaa aaaaaaaaaa aaaaaaaaaa aaaa           54

<210> SEQ ID NO 3
<211> LENGTH: 23
<212> TYPE: DNA
<213> ORGANISM: Artificial Sequence
<220> FEATURE:
<223> OTHER INFORMATION: synthetic capture
      oligomer

<400> SEQUENCE: 3
gctggaataa cttctgcttc tat                                             23

<210> SEQ ID NO 4
<211> LENGTH: 56
<212> TYPE: DNA
<213> ORGANISM: Artificial Sequence
<220> FEATURE:
<223> OTHER INFORMATION: synthetic capture oligomer with 3' tail
      sequence
<220> FEATURE:
<221> NAME/KEY: misc_structure
<222> LOCATION: (24)..(56)
<223> OTHER INFORMATION: 3' tail sequence

<400> SEQUENCE: 4
gctggaataa cttctgcttc tattttaaaa aaaaaaaaaa aaaaaaaaaa aaaaaa         56

<210> SEQ ID NO 5
<211> LENGTH: 24
<212> TYPE: DNA
<213> ORGANISM: Artificial Sequence
```

```
<220> FEATURE:
<223> OTHER INFORMATION: synthetic capture
      oligomer

<400> SEQUENCE: 5
tctgctgtcc ctgtaataaa cccg                                             24

<210> SEQ ID NO 6
<211> LENGTH: 57
<212> TYPE: DNA
<213> ORGANISM: Artificial Sequence
<220> FEATURE:
<223> OTHER INFORMATION: synthetic capture oligomer with 3' tail
      sequence
<220> FEATURE:
<221> NAME/KEY: misc_structure
<222> LOCATION: (25)..(57)
<223> OTHER INFORMATION: 3' tail sequence

<400> SEQUENCE: 6
tctgctgtcc ctgtaataaa cccgtttaaa aaaaaaaaaa aaaaaaaaaa aaaaaa         57

<210> SEQ ID NO 7
<211> LENGTH: 23
<212> TYPE: DNA
<213> ORGANISM: Artificial Sequence
<220> FEATURE:
<223> OTHER INFORMATION: synthetic amplification oligomer for HIV-1
      LTR region

<400> SEQUENCE: 7
cgggcgccac tgctagagat ttt                                              23

<210> SEQ ID NO 8
<211> LENGTH: 50
<212> TYPE: DNA
<213> ORGANISM: Artificial Sequence
<220> FEATURE:
<223> OTHER INFORMATION: synthetic amplification oligomer with 5'
      promoter sequence for HIV-1 LTR region
<220> FEATURE:
<221> NAME/KEY: promoter
<222> LOCATION: (1)..(27)

<400> SEQUENCE: 8
aatttaatac gactcactat agggagacgg gcgccactgc tagagtttt                  50

<210> SEQ ID NO 9
<211> LENGTH: 18
<212> TYPE: DNA
<213> ORGANISM: Artificial Sequence
<220> FEATURE:
<223> OTHER INFORMATION: synthetic amplification oligomer for
      HIV-1 LTR region

<400> SEQUENCE: 9
gcctcaataa agcttgcc                                                    18

<210> SEQ ID NO 10
<211> LENGTH: 19
<212> TYPE: DNA
<213> ORGANISM: Artificial Sequence
<220> FEATURE:
<223> OTHER INFORMATION: synthetic amplification oligomer for HIV-1
      pol sequence

<400> SEQUENCE: 10
acagcagtac aaatggcag                                                   19
```

<210> SEQ ID NO 11
<211> LENGTH: 23
<212> TYPE: DNA
<213> ORGANISM: Artificial Sequence
<220> FEATURE:
<223> OTHER INFORMATION: synthetic amplification oligomer for HIV-1
      pol sequence

<400> SEQUENCE: 11
acaaatggca gtattcatcc aca                                         23

<210> SEQ ID NO 12
<211> LENGTH: 28
<212> TYPE: DNA
<213> ORGANISM: Artificial Sequence
<220> FEATURE:
<223> OTHER INFORMATION: synthetic amplification oligomer for HIV-1
      pol sequence

<400> SEQUENCE: 12
gtttgtatgt ctgttgctat tatgtcta                                    28

<210> SEQ ID NO 13
<211> LENGTH: 55
<212> TYPE: DNA
<213> ORGANISM: Artificial Sequence
<220> FEATURE:
<223> OTHER INFORMATION: synthetic amplification oligomer with 5'
      promoter sequence for HIV-1 pol sequence
<220> FEATURE:
<221> NAME/KEY: promoter
<222> LOCATION: (1)..(27)

<400> SEQUENCE: 13
aatttaatac gactcactat agggagagtt tgtatgtctg ttgctattat gtcta       55

<210> SEQ ID NO 14
<211> LENGTH: 23
<212> TYPE: DNA
<213> ORGANISM: Artificial Sequence
<220> FEATURE:
<223> OTHER INFORMATION: synthetic amplification oligomer for HIV-1
      pol sequence

<400> SEQUENCE: 14
gtttgtatgt ctgttgctat tat                                         23

<210> SEQ ID NO 15
<211> LENGTH: 50
<212> TYPE: DNA
<213> ORGANISM: Artificial Sequence
<220> FEATURE:
<223> OTHER INFORMATION: synthetic amplification oligomer with 5'
      promoter sequence for HIV-1 pol sequence
<220> FEATURE:
<221> NAME/KEY: promoter
<222> LOCATION: (1)..(27)

<400> SEQUENCE: 15
aatttaatac gactcactat agggagagtt tgtatgtctg ttgctattat              50

<210> SEQ ID NO 16
<211> LENGTH: 20
<212> TYPE: DNA
<213> ORGANISM: Artificial Sequence
<220> FEATURE:
<223> OTHER INFORMATION: synthetic oligomer probe

```
<220> FEATURE:
<221> NAME/KEY: modified_base
<222> LOCATION: (7)..(7)
<223> OTHER INFORMATION: inosine
<220> FEATURE:
<221> NAME/KEY: misc_feature
<222> LOCATION: (7)..(7)
<223> OTHER INFORMATION: n is a, c, g, or t

<400> SEQUENCE: 16
ctggtancta gagatccctc                                              20

<210> SEQ ID NO 17
<211> LENGTH: 22
<212> TYPE: DNA
<213> ORGANISM: Artificial Sequence
<220> FEATURE:
<223> OTHER INFORMATION: synthetic oligomer probe

<400> SEQUENCE: 17 ccacaattt aaaagaaaag gg                                            22

<210> SEQ ID NO 18
<211> LENGTH: 17
<212> TYPE: DNA
<213> ORGANISM: Artificial Sequence
<220> FEATURE:
<223> OTHER INFORMATION: synthetic oligomer probe
<220> FEATURE:
<221> NAME/KEY: modified_base
<222> LOCATION: (8)..(8)
<223> OTHER INFORMATION: inosine
<220> FEATURE:
<221> NAME/KEY: misc_feature
<222> LOCATION: (8)..(8)
<223> OTHER INFORMATION: n is a, c, g, or t

<400> SEQUENCE: 18
ggattggngg gtacagt                                                 17

<210> SEQ ID NO 19
<211> LENGTH: 22
<212> TYPE: DNA
<213> ORGANISM: Artificial Sequence
<220> FEATURE:
<223> OTHER INFORMATION: synthetic capture oligomer

<400> SEQUENCE: 19
acaaccatcc aaargtcagt gg                                           22

<210> SEQ ID NO 20
<211> LENGTH: 52
<212> TYPE: DNA
<213> ORGANISM: Artificial Sequence
<220> FEATURE:
<223> OTHER INFORMATION: synthetic capture oligomer with 3' tail
      sequence
<220> FEATURE:
<221> NAME/KEY: misc_structure
<222> LOCATION: (23)..(52)
<223> OTHER INFORMATION: 3' tail sequence

<400> SEQUENCE: 20
acaaccatcc aaargtcagt ggaaaaaaaa aaaaaaaaaa aaaaaaaaaa aa           52

<210> SEQ ID NO 21
<211> LENGTH: 19
<212> TYPE: DNA
<213> ORGANISM: Artificial Sequence
```

```
<220> FEATURE:
<223> OTHER INFORMATION: synthetic amplification oligomer for HIV-1
      LTR region

<400> SEQUENCE: 21
cctgttcggg cgccactgc                                                      19

<210> SEQ ID NO 22
<211> LENGTH: 43
<212> TYPE: DNA
<213> ORGANISM: Artificial Sequence
<220> FEATURE:
<223> OTHER INFORMATION: synthetic amplification oligomer with 5'
      promoter sequence for HIV-1 LTR region
<220> FEATURE:
<221> NAME/KEY: promoter
<222> LOCATION: (1)..(24)

<400> SEQUENCE: 22
ttaatacgac tcactatagg gagacctgtt cgggcgccac tgc                            43

<210> SEQ ID NO 23
<211> LENGTH: 21
<212> TYPE: DNA
<213> ORGANISM: Artificial Sequence
<220> FEATURE:
<223> OTHER INFORMATION: synthetic amplification oligomer for HIV-1
      LTR region
<400> SEQUENCE: 23
ggcgccactg ctagagattt t                                                   21

<210> SEQ ID NO 24
<211> LENGTH: 48
<212> TYPE: DNA
<213> ORGANISM: Artificial Sequence
<220> FEATURE:
<223> OTHER INFORMATION: synthetic amplification oligomer with 5'
      promoter sequence for HIV-1 LTR region
<220> FEATURE:
<221> NAME/KEY: promoter
<222> LOCATION: (1)..(27)

<400> SEQUENCE: 24
aatttaatac gactcactat agggagaggc gccactgcta gagatttt                      48

<210> SEQ ID NO 25
<211> LENGTH: 24
<212> TYPE: DNA
<213> ORGANISM: Artificial Sequence
<220> FEATURE:
<223> OTHER INFORMATION: synthetic amplification oligomer for HIV-1
      LTR region

<400> SEQUENCE: 25
cgggcgccac tgctagagat tttc                                                24

<210> SEQ ID NO 26
<211> LENGTH: 51
<212> TYPE: DNA
<213> ORGANISM: Artificial Sequence
<220> FEATURE:
<223> OTHER INFORMATION: synthetic amplification oligomer with 5'
      promoter sequence for HIV-1 LTR region
<220> FEATURE:
<221> NAME/KEY: promoter
<222> LOCATION: (1)..(27)

<400> SEQUENCE: 26
```

-continued aatttaatac gactcactat agggagacgg gcgccactgc tagagatttt c     51

<210> SEQ ID NO 27
<211> LENGTH: 23
<212> TYPE: DNA
<213> ORGANISM: Artificial Sequence
<220> FEATURE:
<223> OTHER INFORMATION: synthetic amplification oligomer for HIV-1
      LTR region

<400> SEQUENCE: 27
gggcgccact gctagagatt ttc     23

<210> SEQ ID NO 28
<211> LENGTH: 49
<212> TYPE: DNA
<213> ORGANISM: Artificial Sequence
<220> FEATURE:
<223> OTHER INFORMATION: synthetic amplification oligomer with 5'
      promoter sequence for HIV-1 LTR region
<220> FEATURE:
<221> NAME/KEY: promoter
<222> LOCATION: (1)..(27)

<400> SEQUENCE: 28
aatttaatac gactcactat agggagaggc gccactgcta gagattttc     49

<210> SEQ ID NO 29
<211> LENGTH: 21
<212> TYPE: DNA
<213> ORGANISM: Artificial Sequence
<220> FEATURE:
<223> OTHER INFORMATION: synthetic amplification oligomer for HIV-1
      LTR region

<400> SEQUENCE: 29
gttcgggcgc cactgctaga g     21

<210> SEQ ID NO 30
<211> LENGTH: 48
<212> TYPE: DNA
<213> ORGANISM: Artificial Sequence
<220> FEATURE:
<223> OTHER INFORMATION: synthetic amplification oligomer with 5'
      promoter sequence for HIV-1 LTR region
<220> FEATURE:
<221> NAME/KEY: promoter
<222> LOCATION: (1)..(27)

<400> SEQUENCE: 30
aatttaatac gactcactat agggagagtt cgggcgccac tgctagag     48

<210> SEQ ID NO 31
<211> LENGTH: 21
<212> TYPE: DNA
<213> ORGANISM: Artificial Sequence
<220> FEATURE:
<223> OTHER INFORMATION: synthetic amplification oligomer for HIV-1
      LTR region

<400> SEQUENCE: 31
ctgttcgggc gccactgcta g     21

<210> SEQ ID NO 32
<211> LENGTH: 47
<212> TYPE: DNA
<213> ORGANISM: Artificial Sequence
<220> FEATURE:

```
<223> OTHER INFORMATION: synthetic amplification oligomer with 5'
      promoter sequence for  HIV-1 LTR region
<220> FEATURE:
<221> NAME/KEY: promoter
<222> LOCATION: (1)..(26)

<400> SEQUENCE: 32
atttaatacg actcactata gggagactgt tcgggcgcca ctgctag          47

<210> SEQ ID NO 33
<211> LENGTH: 24
<212> TYPE: DNA
<213> ORGANISM: Artificial Sequence
<220> FEATURE:
<223> OTHER INFORMATION: synthetic amplification oligomer for HIV-1
      LTR region

<400> SEQUENCE: 33
gcaagccgag tcctgcgtcg agag                                   24

<210> SEQ ID NO 34
<211> LENGTH: 51
<212> TYPE: DNA
<213> ORGANISM: Artificial Sequence
<220> FEATURE:
<223> OTHER INFORMATION: synthetic amplification oligomer with 5'
      promoter sequence for HIV-1 LTR region
<220> FEATURE:
<221> NAME/KEY: promoter
<222> LOCATION: (1)..(27)

<400> SEQUENCE: 34
aatttaatac gactcactat agggagagca agccgagtcc tgcgtcgaga g     51

<210> SEQ ID NO 35
<211> LENGTH: 26
<212> TYPE: DNA
<213> ORGANISM: Artificial Sequence
<220> FEATURE:
<223> OTHER INFORMATION: synthetic amplification oligomer for HIV-1
      LTR region

<400> SEQUENCE: 35
gcttaagcct caataaagct tgccctt                                26

<210> SEQ ID NO 36
<211> LENGTH: 23
<212> TYPE: DNA
<213> ORGANISM: Artificial Sequence
<220> FEATURE:
<223> OTHER INFORMATION: synthetic amplification oligomer for HIV-1
      LTR region

<400> SEQUENCE: 36
gcctcaataa agcttgcctt gag                                    23

<210> SEQ ID NO 37
<211> LENGTH: 23
<212> TYPE: DNA
<213> ORGANISM: Artificial Sequence
<220> FEATURE:
<223> OTHER INFORMATION: synthetic amplification oligomer for HIV-1
      LTR region

<400> SEQUENCE: 37
gcttaagcct caataaagct tgc                                    23
```

```
<210> SEQ ID NO 38
<211> LENGTH: 21
<212> TYPE: DNA
<213> ORGANISM: Artificial Sequence
<220> FEATURE:
<223> OTHER INFORMATION: synthetic amplification oligomer for HIV-1
      LTR region

<400> SEQUENCE: 38
ctgcttaagc ctcaataaag c                                            21

<210> SEQ ID NO 39
<211> LENGTH: 20
<212> TYPE: DNA
<213> ORGANISM: Artificial Sequence
<220> FEATURE:
<223> OTHER INFORMATION: synthetic oligomer probe
<220> FEATURE:
<221> NAME/KEY: modified_base
<222> LOCATION: (6)..(7)
<223> OTHER INFORMATION: inosine
<220> FEATURE:
<221> NAME/KEY: misc_feature
<222> LOCATION: (6)..(7)
<223> OTHER INFORMATION: n is a, c, g, or t

<400> SEQUENCE: 39
ctggtnncta gagatccctc                                              20

<210> SEQ ID NO 40
<211> LENGTH: 20
<212> TYPE: DNA
<213> ORGANISM: Artificial Sequence
<220> FEATURE:
<223> OTHER INFORMATION: synthetic oligomer probe

<400> SEQUENCE: 40
ggtarctaga gatccctcag                                              20

<210> SEQ ID NO 41
<211> LENGTH: 20
<212> TYPE: DNA
<213> ORGANISM: Artificial Sequence
<220> FEATURE:
<223> OTHER INFORMATION: synthetic oligomer probe

<400> SEQUENCE: 41
gactctggta actagagatc                                              20

<210> SEQ ID NO 42
<211> LENGTH: 16
<212> TYPE: DNA
<213> ORGANISM: Artificial Sequence
<220> FEATURE:
<223> OTHER INFORMATION: synthetic amplification oligomer for HIV-1
      pol sequence

<400> SEQUENCE: 42
acagcagtac aaatgg                                                  16

<210> SEQ ID NO 43
<211> LENGTH: 51
<212> TYPE: DNA
<213> ORGANISM: Artificial Sequence
<220> FEATURE:
<223> OTHER INFORMATION: synthetic amplification oligomer with 5'
      promoter sequence for HIV-1 pol sequence
<220> FEATURE:
<221> NAME/KEY: promoter
```

```
<222> LOCATION: (1)..(27)

<400> SEQUENCE: 43
aatttaatac gactcactat agggagagta tgtctgttgc tattatgtct a       51

<210> SEQ ID NO 44
<211> LENGTH: 51
<212> TYPE: DNA
<213> ORGANISM: Artificial Sequence
<220> FEATURE:
<223> OTHER INFORMATION: synthetic amplification oligomer with 5'
      promoter sequence for HIV-1 pol sequence
<220> FEATURE:
<221> NAME/KEY: promoter
<222> LOCATION: (1)..(27)

<400> SEQUENCE: 44
aatttaatac gactcactat agggagaagt ttgtatgtct gttgctatta t       51

<210> SEQ ID NO 45
<211> LENGTH: 54
<212> TYPE: DNA
<213> ORGANISM: Artificial Sequence
<220> FEATURE:
<223> OTHER INFORMATION: synthetic capture oligomer with 3' tail
      sequence
<220> FEATURE:
<221> NAME/KEY: misc_structure
<222> LOCATION: (12)..(54)
<223> OTHER INFORMATION: 3' tail sequence

<400> SEQUENCE: 45
actgacgcac tcgcacccat ctttaaaaaa aaaaaaaaaa aaaaaaaaaa aaaa    54

<210> SEQ ID NO 46
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: modified_base
<222> LOCATION: (26)..(26)
<223> OTHER INFORMATION: inosine
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: modified_base
<222> LOCATION: (29)..(29)
<223> OTHER INFORMATION: inosine
<220> FEATURE:
<221> NAME/KEY: misc_feature
<222> LOCATION: (29)..(29)
<223> OTHER INFORMATION: n is a, c, g, t or u

<400> SEQUENCE: 46
tcatucacaa ttttaaaaga aaaggnggna                               30

<210> SEQ ID NO 47
<211> LENGTH: 30
<212> TYPE: DNA
<213> ORGANISM: Artificial Sequence
<220> FEATURE:
<223> OTHER INFORMATION: synthetic oligomer probe

<400> SEQUENCE: 47
ccacaatttt aaagaaaaag ggggattgg                                30
```

<210> SEQ ID NO 48
<211> LENGTH: 30
<212> TYPE: DNA
<213> ORGANISM: Artificial Sequence
<220> FEATURE:
<223> OTHER INFORMATION: synthetic oligomer probe

<400> SEQUENCE: 48
gggtacagtg caggggaaag aatagtagac        30

<210> SEQ ID NO 49
<211> LENGTH: 22
<212> TYPE: DNA
<213> ORGANISM: Artificial Sequence
<220> FEATURE:
<223> OTHER INFORMATION: synthetic oligomer probe

<400> SEQUENCE: 49
gggtacagtg caggggaaag aa        22

<210> SEQ ID NO 50
<211> LENGTH: 18
<212> TYPE: DNA
<213> ORGANISM: Artificial Sequence
<220> FEATURE:
<223> OTHER INFORMATION: synthetic oligomer probe
<220> FEATURE:
<221> NAME/KEY: modified_base
<222> LOCATION: (9)..(9)
<223> OTHER INFORMATION: inosine
<220> FEATURE:
<221> NAME/KEY: misc_feature
<222> LOCATION: (9)..(9)
<223> OTHER INFORMATION: n is a, c, g, or t

<400> SEQUENCE: 50
agaaaaggng ggattggg        18

<210> SEQ ID NO 51
<211> LENGTH: 20
<212> TYPE: DNA
<213> ORGANISM: Artificial Sequence
<220> FEATURE:
<223> OTHER INFORMATION: synthetic oligomer probe
<220> FEATURE:
<221> NAME/KEY: modified_base
<222> LOCATION: (4)..(4)
<223> OTHER INFORMATION: inosine
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: modified_base
<222> LOCATION: (13)..(13)
<223> OTHER INFORMATION: inosine
<220> FEATURE:
<221> NAME/KEY: misc_feature
<222> LOCATION: (13)..(13)
<223> OTHER INFORMATION: n is a, c, g, or t

<400> SEQUENCE: 51
aggngggatt ggngggtaca        20

<210> SEQ ID NO 52
<211> LENGTH: 20
<212> TYPE: DNA
<213> ORGANISM: Artificial Sequence
<220> FEATURE:
<223> OTHER INFORMATION: synthetic oligomer probe

```
<220> FEATURE:
<221> NAME/KEY: modified_base
<222> LOCATION: (3)..(3)
<223> OTHER INFORMATION: inosine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (11)..(11)
<223> OTHER INFORMATION: inosine
<220> FEATURE:
<221> NAME/KEY: misc_feature
<222> LOCATION: (11)..(11)
<223> OTHER INFORMATION: n is a, c, g, or t

<400> SEQUENCE: 52
ggnggattgg ngggtacagt                                           20

<210> SEQ ID NO 53
<211> LENGTH: 19
<212> TYPE: DNA
<213> ORGANISM: Artificial Sequence
<220> FEATURE:
<223> OTHER INFORMATION: synthetic oligomer probe
<220> FEATURE:
<221> NAME/KEY: modified_base
<222> LOCATION: (9)..(9)
<223> OTHER INFORMATION: inosine
<220> FEATURE:
<221> NAME/KEY: misc_feature
<222> LOCATION: (9)..(9)
<223> OTHER INFORMATION: n is a, c, g, or t

<400> SEQUENCE: 53
gggattggng ggtacagtg                                            19

<210> SEQ ID NO 54
<211> LENGTH: 20
<212> TYPE: DNA
<213> ORGANISM: Artificial Sequence
<220> FEATURE:
<223> OTHER INFORMATION: synthetic oligomer probe

<400> SEQUENCE: 54
caggggaaag aatagtagac                                           20

<210> SEQ ID NO 55
<211> LENGTH: 17
<212> TYPE: DNA
<213> ORGANISM: Artificial Sequence
<220> FEATURE:
<223> OTHER INFORMATION: synthetic oligomer probe

<400> SEQUENCE: 55
caggggaaag aatagta                                              17

<210> SEQ ID NO 56
<211> LENGTH: 18
<212> TYPE: DNA
<213> ORGANISM: Artificial Sequence
<220> FEATURE:
<223> OTHER INFORMATION: synthetic oligomer probe

<400> SEQUENCE: 56
ggggaaagaa tagtagac                                             18

<210> SEQ ID NO 57
```

```
-continued

<211> LENGTH: 22
<212> TYPE: DNA
<213> ORGANISM: Artificial Sequence
<220> FEATURE:
<223> OTHER INFORMATION: synthetic capture oligomer

<400> SEQUENCE: 57
actgacgcac tcgcacccat ct                                              22
```